(12) United States Patent
Kamogawa et al.

(10) Patent No.: US 11,795,064 B2
(45) Date of Patent: Oct. 24, 2023

(54) POLYMETALLOXANE, METHOD FOR PRODUCING SAME, COMPOSITION THEREOF, CURED FILM AND METHOD FOR PRODUCING SAME, AND MEMBERS AND ELECTRONIC COMPONENTS PROVIDED WITH SAME

(71) Applicant: TORAY INDUSTRIES, INC., Tokyo (JP)

(72) Inventors: Masao Kamogawa, Otsu (JP); Mitsuhito Suwa, Otsu (JP); Hiroko Mitsui, Otsu (JP); Miki Nakamichi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 159 days.

(21) Appl. No.: 15/772,881

(22) PCT Filed: Nov. 17, 2016

(86) PCT No.: PCT/JP2016/084138
§ 371 (c)(1),
(2) Date: May 2, 2018

(87) PCT Pub. No.: WO2017/090512
PCT Pub. Date: Jun. 1, 2017

(65) Prior Publication Data
US 2018/0327275 A1 Nov. 15, 2018

(30) Foreign Application Priority Data

Nov. 26, 2015 (JP) ................................. 2015-230446
Feb. 26, 2016 (JP) ................................. 2016-035370
Feb. 26, 2016 (JP) ................................. 2016-035371
Apr. 27, 2016 (JP) ................................. 2016-088895

(51) Int. Cl.
| | |
|---|---|
| *C01G 25/00* | (2006.01) |
| *H05B 33/22* | (2006.01) |
| *C08L 85/00* | (2006.01) |
| *C08G 79/00* | (2006.01) |
| *C08K 3/22* | (2006.01) |
| *G02B 1/11* | (2015.01) |
| *B32B 9/00* | (2006.01) |
| *H05B 33/28* | (2006.01) |
| *C07F 7/08* | (2006.01) |
| *H10K 50/00* | (2023.01) |
| *G02B 5/28* | (2006.01) |
| *A61K 51/04* | (2006.01) |

(52) U.S. Cl.
CPC ........... *C01G 25/006* (2013.01); *B32B 9/00* (2013.01); *C07F 7/0836* (2013.01); *C08G 79/00* (2013.01); *C08K 3/22* (2013.01); *C08L 85/00* (2013.01); *G02B 1/11* (2013.01); *G02B 5/28* (2013.01); *H05B 33/22* (2013.01); *H05B 33/28* (2013.01); *H10K 50/00* (2023.02); *A61K 51/0478* (2013.01)

(58) Field of Classification Search
None
See application file for complete search history.

(56) References Cited

U.S. PATENT DOCUMENTS

| | | | | |
|---|---|---|---|---|
| 3,152,999 | A | * 10/1964 | Rust ....................... | C08G 79/10 528/26 |
| 3,530,078 | A | * 9/1970 | Roberts .................. | C08G 79/10 528/9 |
| 4,273,420 | A | 6/1981 | Watanabe et al. | |
| 4,904,059 | A | 2/1990 | Torigoe | |
| 5,596,060 | A | * 1/1997 | Kushibiki .............. | C08G 79/00 528/15 |
| 8,512,870 | B2 | * 8/2013 | Shin ....................... | C08G 77/02 428/447 |
| 9,335,208 | B2 | 5/2016 | Nishimura | |
| 2006/0239902 | A1 | 10/2006 | Kimura et al. | |
| 2015/0284539 | A1 | 10/2015 | Kurita et al. | |
| 2015/0370358 | A1 | 12/2015 | Araki et al. | |

FOREIGN PATENT DOCUMENTS

| | | |
|---|---|---|
| EP | 2540780 A1 | 1/2013 |
| JP | 5562428 A | 5/1980 |

(Continued)

OTHER PUBLICATIONS

Wang, Y., et al., "Synthesis of Polymetalloxanes and Their Properties as Gate Insulator for Organic Thin Film Transistors", Macromolecular Research, pp. 899-904 (Year: 2013).*

(Continued)

*Primary Examiner* — Michael G. Hartley
*Assistant Examiner* — Lance W Rider
(74) *Attorney, Agent, or Firm* — RatnerPrestia

(57) ABSTRACT

Disclosed is a polymetalloxane including a constituent unit represented by the following general formula (1), which stably exists in a transparent and uniform state in a solution and can form a homogeneous cured film:

[Chemical Formula 1]

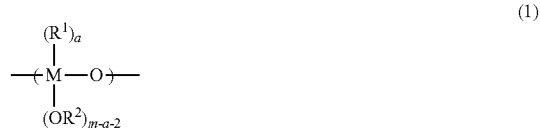

(1)

wherein $R^1$ is an organic group and at least one of $R^1$ is an ($R^3{}_3SiO$—) group, $R^3$ is optionally selected from specific groups, $R^2$ is optionally selected from specific groups, when plural $R^1$, $R^2$, and $R^3$ exist, they may be the same or different, M represents a specific metal atom, m is an integer indicating a valence of a metal atom M, and a is an integer of 1 to (m−2).

17 Claims, 1 Drawing Sheet

(56) References Cited

FOREIGN PATENT DOCUMENTS

| | | | |
|---|---|---|---|
| JP | 01129032 A | 5/1989 | |
| JP | 01205122 A | 8/1989 | |
| JP | 08240800 A | 9/1996 | |
| JP | 2003165841 A | 6/2003 | |
| JP | 2003165916 A | 6/2003 | |
| JP | 2008156280 A | 7/2008 | |
| JP | 2009173910 A | 8/2009 | |
| JP | 2010086684 A | 4/2010 | |
| JP | 2010152809 A | 7/2010 | |
| JP | 2012097180 A | 5/2012 | |
| JP | 2012223711 A | 11/2012 | |
| JP | 2014122135 A | 7/2014 | |
| JP | 2015003896 A | 1/2015 | |
| JP | 2015113463 A | 6/2015 | |
| JP | 2015209466 A | 11/2015 | |
| JP | 2015212329 A | 11/2015 | |
| JP | 6033000 B2 | 11/2016 | |
| RU | 2444540 C1 | 3/2012 | |
| WO | 0160141 A2 | 8/2001 | |
| WO | 2014119372 A1 | 8/2014 | |
| WO | 2015156703 A | 10/2015 | |

OTHER PUBLICATIONS

Polysilicates, "Polysilicates", accessed from: https://www.wou.edu/las/physci/ch412/poly_si.htm, accessed on: Oct. 11, 2019, pp. 1-8 (Year: 2019).*

Sokol, A., et al., "Local States in Microporous Silica and Aluminum Silicate Materials. 1. Modeling Structure, Formation, and Transformation of Common Hydrogen Containing Defects" J. Phys. Chem. B., pp. 6163-6177 (Year: 2002).*

Cho, A., et al., "Synthesis of titania- and silica-polymer hybrid materials and their application as refractive index-matched layers in touch screens" Optical Materials Express, pp. 690-703 (Year: 2015).*

Andrianov, K.A., "Synthesis of New Polymers with Inorganic Chains of Molecules" J. Polymer Sci., pp. 513-524 (Year: 1958).*

Gunji et al., "Studies on the Syntheses of Polymetalloxanes and Their Properties as a Precursor for Amorphous Oxide. V. Preparation and Properties of Polytitanosiloxanes from Silicic Acid and Bis(2,4-Pentanedionato)-titanium Diisopropoxide", Journal of Polymer Science, Part A: Polymer Chemistry, 1991, vol. 29, pp. 941-947.

Extended European Search Report for European Application No. 16868460.3, dated May 28, 2019, 9 pages.

International Search Report and Written Opinion for International Application No. PCT/JP2016/084138, dated Feb. 14, 2017, 7 pages.

* cited by examiner

POLYMETALLOXANE, METHOD FOR PRODUCING SAME, COMPOSITION THEREOF, CURED FILM AND METHOD FOR PRODUCING SAME, AND MEMBERS AND ELECTRONIC COMPONENTS PROVIDED WITH SAME

CROSS REFERENCE TO RELATED APPLICATIONS

This is the U.S. National Phase application of PCT/JP2016/084138, filed Nov. 17, 2016, which claims priority to Japanese Patent Application No. 2015-230446, filed Nov. 26, 2015, Japanese Patent Application No. 2016-035370, filed Feb. 26, 2016, Japanese Patent Application No. 2016-035371, filed Feb. 26, 2016, and Japanese Patent Application No. 2016-088895, filed Apr. 27, 2016, the disclosures of these applications being incorporated herein by reference in their entireties for all purposes.

TECHNICAL FIELD OF THE INVENTION

The present invention relates to a polymetalloxane, a method for producing same, a composition thereof, a cured film and a method for producing same, and members and electronic components provided with same.

BACKGROUND OF THE INVENTION

A film made of a metal oxide has properties such as high heat resistance, high transparency, high refractive index, and the like and is expected to have properties useful for various applications.

There has been known, as a method for forming such a film, a method of forming a film of titanium oxide or zirconium oxide by a vapor phase method such as chemical vapor deposition (CVD). However, because of low film forming rate, it is difficult for the vapor phase method such as CVD to obtain a film thickness that can be industrially used.

Meanwhile, there has been proposed a method in which a metal alkoxide is hydrolyzed in a solvent, followed by polycondensation to form a polymetalloxane, and the polymetalloxane is coated and cured to obtain a high refractive index thin film. However, when the metal alkoxide is hydrolyzed, the hydrolyzate aggregates and becomes insoluble in the organic solvent. For this reason, a polymetalloxane, which stably exists in a transparent and uniform state in a solution and can form a homogeneous cured film, has not been industrialized at present.

In the past literatures, there, has been reported technology in which aggregation of a hydrolysate is prevented by carefully carrying out the hydrolysis under special conditions (see, for example, Patent Literatures 1 and 2).

CITATION LIST

Patent Literature

[Patent Literature 1] JP 1-129032 A
[Patent Literature 2] JP 2015-3896 A

SUMMARY OF THE INVENTION

As a method of hydrolyzing a metal alkoxide in a solvent, technology mentioned in Patent Literature 1 is a method in which the temperature of a metal alkoxide solution is maintained at 70° C. and water for hydrolysis is added in the amount of 1 mol or more and 1.7-fold mols or less based on 1 mol of a titanium alkoxide to obtain a ladder-like polytitanoxane which is soluble in an organic solvent. However, such a method had a problem that the addition of water at a temperature lower than 70° C. or an increase in amount of water leads to precipitation due to aggregation of the hydrolysate. Because of low degree of the hydrolysis, numerous alkoxy groups remain in the resulting polytitanoxane and the alkoxy group is hydrolyzed by moisture in the air during formation of a coating film, thus failing to form a homogeneous film by crack generation due to the elimination.

Technology mentioned in Patent Literature 2 is technology in which a titanium compound is reacted with water in an alcohol solution in the presence of a special hydrochloride to produce a titanium compound oligomer. However, such a method also had a problem that an increase in amount of water leads to precipitation due to aggregation of the hydrolysate. Therefore, a high molecular weight polymetalloxane cannot be obtained, leading to crack generation during formation of a coating film, thus failing to form a homogeneous film.

An object of the present invention is to provide a polymetalloxane which stably exists in a transparent and uniform state in a solution and can form a homogeneous cured film.

The present invention is directed to a polymetalloxane including a constituent unit represented by the following general formula (1):

[Chemical Formula 1]

wherein $R^1$ is an organic group, at least one of $R^1$ is an ($R^3{}_3$SiO—) group, $R^3$ is optionally selected from a hydroxy group, an alkyl group having 1 to 12 carbon atoms, an alicyclic alkyl group having 5 to 12 carbon atoms, an alkoxy group having 1 to 12 carbon atoms, an aromatic group having 6 to 30 carbon atoms, a group having a siloxane bond, or a group having a metalloxane bond, $R^2$ is optionally selected from a hydrogen atom, an alkyl group having 1 to 12 carbon atoms, or a group having a metalloxane bond, when plural $R^1$, $R^2$, and $R^3$ exist, they may be the same or different, M represents a metal atom selected from the group consisting of Al, Ti, V, Cr, Mn, Fe, Co, Ni, Cu, Zn, Ga, Ge, Zr, Nb, Mo, Ru, Rh, Pd, Ag, In, Sn, Sb, Hf, Ta, W, Re, Os, Ir, Pt, Au, Tl, and Bi, m is an integer indicating a valence of a metal atom M, and a is an integer of 1 to (m−2).

The present invention is directed to, in another aspect, a method for producing a polymetalloxane, which including the step of polycondensing a compound represented by the following general formula (2):

[Chemical Formula 2]

wherein R⁴ is optionally selected from a hydroxy group, an alkyl group having 1 to 12 carbon atoms, an alicyclic alkyl group having 5 to 12 carbon atoms, an alkoxy group having 1 to 12 carbon atoms, or an aromatic group having 6 to 30 carbon atoms, $R^5$ is optionally selected from a hydrogen atom or an alkyl group having 1 to 12 carbon atoms, when plural $R^4$ and $R^5$ exist, they may be the same or different, M represents a metal atom selected from the group consisting of Al, Ti, V, Cr, Mn, Fe, Co, Ni, Cu, Zn, Ga, Ge, Zr, Nb, Mo, Ru, Rh, Pd, Ag, In, Sn, Sb, Hf, Ta, W, Re, Os, Ir, Pt, Au, Tl, and Bi, m is an integer indicating a valence of a metal atom M, and n is an integer of 1 to (m−1), or a hydrolysate thereof.

Advantageous Effects of Invention

The polymetalloxane of the present invention stably exists in a transparent and uniform state in a solution. According to the polymetalloxane of the present invention, it is possible to provide a cured film having high transparency and high refractive index.

Figure 1:
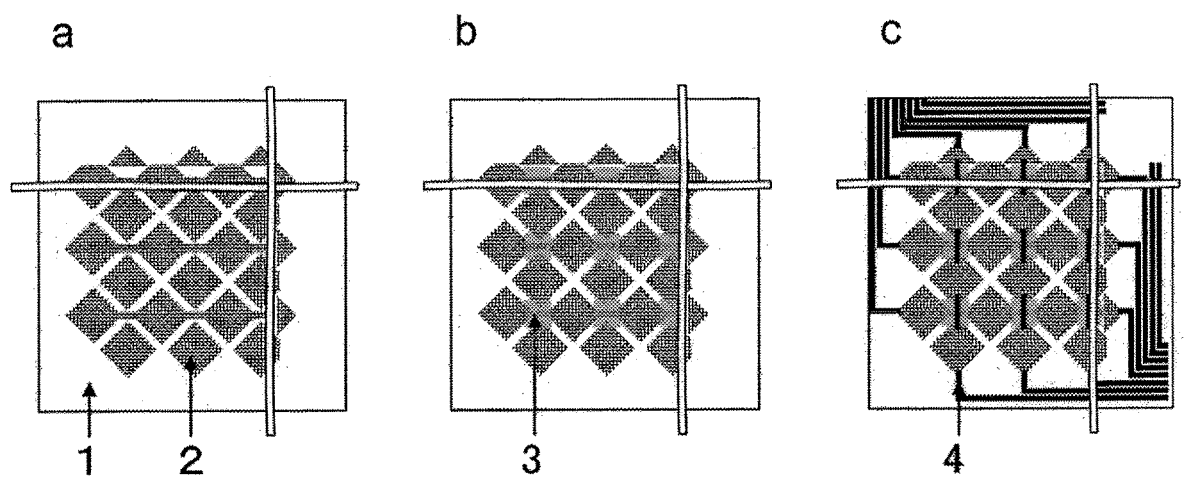
FIG. 1A-C are schematic views showing the production process respectively of a transparent conductive film pattern, a transparent insulating film, and wiring.

DETAILED DESCRIPTION OF CERTAIN EMBODIMENTS OF THE INVENTION (Polymetalloxane)

The present invention is directed to a polymetalloxane including a constituent unit represented by the following general formula (1).

[Chemical Formula 3]

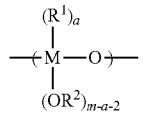

(1)

$R^1$ is an organic group, at least one of $R^1$ is an ($R^3{}_3$SiO—) group. $R^3$ is optionally selected from a hydroxy group, an alkyl group having 1 to 12 carbon atoms, an alicyclic alkyl group having 5 to 12 carbon atoms, an alkoxy group having 1 to 12 carbon atoms, an aromatic group having 6 to 30 carbon atoms, a group having a siloxane bond, or a group having a metalloxane bond. $R^2$ is optionally selected from a hydrogen atom, an alkyl group having 1 to 12 carbon atoms, or a group having a metalloxane bond. When plural $R^1$, $R^2$, and $R^3$ exist, they may be the same or different. M represents a metal atom selected from the group consisting of Al, Ti, V, Cr, Mn, Fe, Co, Ni, Cu, Zn, Ga, Ge, Zr, Nb, Mo, Ru, Rh, Pd, Ag, In, Sn, Sb, Hf, Ta, W, Re, Os, Ir, Pt, Au, Tl, and Bi. m is an integer indicating a valence of a metal atom M, and a is an integer of 1 to (m−2).

The organic group represented by $R^1$ is preferably a hydroxy group, an alkyl group having 1 to 12 carbon atoms, an alicyclic alkyl group having 5 to 12 carbon atoms, an alkoxy group having 1 to 12 carbon atoms, an aromatic group having 6 to 30 carbon atoms, an ($R^3{}_3$SiO—) group, a group having a siloxane bond, or a group having a metalloxane bond.

Examples of the alkyl group having 1 to 12 carbon atoms include a methyl group, an ethyl group, a propyl group, an isopropyl group, a butyl group, an isobutyl group, a s-butyl group, a t-butyl group, a pentyl group, a hexyl group, a heptyl group, an octyl group, a 2-ethylhexyl group, a nonyl group, a decyl group, and the like.

Examples of the alicyclic alkyl group having 5 to 12 carbon atoms include a cyclopentyl group, a cyclohexyl group, a cycloheptyl group, a cyclooctyl group, a cyclononyl group, a cyclodecyl group, and the like.

Examples of the alkoxy group having 1 to 12 carbon atoms include a methoxy group, an ethoxy group, a propoxy group, an isopropoxy group, a butoxy group, an isobutoxy group, a s-butoxy group, a t-butoxy group, a pentoxy group, a hexyloxy group, a heptoxy group, an octoxy group, a 2-ethylhexyloxy group, a nonyl group, a decyloxy group, and the like.

Examples of the aromatic group having 6 to 30 carbon atoms include a phenyl group, a phenoxy group, a benzyl group, a phenylethyl group, a naphthyl group, and the like.

The group having a siloxane bond means that it is bonded to another Si. The group having a metalloxane bond indicates that it is bonded to the other M.

These descriptions are also common to the metal compounds represented by the general formulas (2) and (3) described below unless otherwise specified.

The polymetalloxane of the present invention has a constituent unit represented by the general formula (1) as a repeating unit. The polymetalloxane having the constituent unit represented by the general formula (1) has an ($R^3{}_3$SiO—) group, leading to significant improvement in compatibility with other components. Therefore, the polymetalloxane stably exists in an organic solvent.

The polymetalloxane having the constituent unit represented by the general formula (1) has the ($R^3{}_3$SiO—) group, thus enabling release of condensation stress of the polymetalloxane by heating in the step of forming the cured film mentioned later. Therefore, use of the polymetalloxane enables formation of a homogeneous cured film which hardly generates cracking.

Examples of the ($R^3{}_3$SiO—) group include a trihydroxysiloxy group, a trimethylsiloxy group, a triethylsiloxy group, a tripropylsiloxy group, a triisopropylsiloxy group, a tributylsiloxy group, a triisobutylsiloxy group, a tri-s-butylsiloxy group, a tri-t-butylsiloxy group, a tricyclohexylsiloxy group, a trimethoxysiloxy group, a triethoxysiloxy group, a tripropoxysiloxy group, a triisopropoxysiloxy group, a tributoxysiloxy group, a triphenylsiloxy group, a hydroxydiphenylsiloxy group, a methyldiphenylsiloxy group, an ethyldiphenylsiloxy group, a propyldiphenylsiloxy group, a dihydroxy(phenyl)siloxy group, a dimethyl(phenyl)siloxy group, a diethyl(phenyl)siloxy group, a dipropyl(phenyl)siloxy group, a trinaphthylsiloxy group, a hydroxydinaphthylsiloxy group, a methyldinaphthylsiloxy group, an ethyldinaphthylsiloxy group, a propyldinaphthylsiloxy group, a dihydroxy(naphthyl)siloxy group, a dimethyl(naphthyl)siloxy group, a diethyl(naphthyl)siloxy group, a dipropyl(naphthyl)siloxy group, and the like.

From the viewpoint of the heat resistance of the polymetalloxane, $R^3$ is preferably an alkyl group having 1 to 4 carbon atoms or a phenyl group. Specific examples of the alkyl group having 1 to 4 carbon atoms include a methyl group, an ethyl group, a propyl group, an isopropyl group, a butyl group, an isobutyl group, and a t-butyl group.

Examples of preferred ($R^3_3SiO—$) group include a trimethylsiloxy group, a triethylsiloxy group, a tripropylsiloxy group, a triisopropylsiloxy group, a tributylsiloxy group, a triisobutylsiloxy group, a tri-s-butylsiloxy group, a tri-t-butylsiloxy group, a methyldiphenylsiloxy group, an ethyldiphenylsiloxy group, a propyldiphenylsiloxy group, a dihydroxy(phenyl)siloxy group, a dimethyl(phenyl)siloxy group, a diethyl(phenyl)siloxy group, a dipropyl(phenyl)siloxy group, and the like.

When the content of the ($R^3_3SiO—$) group is represented by the ratio of the number of mols of Si atoms to the number of mols of M atoms of the polymetalloxane, it is preferably 1 mol % or more and 250 mol % or less, and more preferably 10 mol % or more and 200 mol % or less. By setting the content of the ($R^3_3SiO—$) group in the above range, the compatibility of the polymetalloxane with other components is further improved. Therefore, the polymetalloxane stably exists particularly in an organic solvent.

At least one of $R^1$ in the polymetalloxane is preferably a hydroxyl group. Inclusion of the hydroxyl group in the polymetalloxane having a structural unit represented by the general formula (1) enables formation of a polymetalloxane excellent in storage stability with a small increase in viscosity even during long-term storage.

When the polymetalloxane has the constituent unit represented by the general formula (1), it is possible to forma cured film mainly composed of a resin containing metal atoms having high electron density in the main chain. Therefore, the density of metal atoms in the cured film can be increased, thus making it possible to easily achieve a high refractive index. When the polymetalloxane has the constituent unit represented by the general formula (1), a dielectric having no free electrons is obtained, thus making it possible to achieve high transparency and heat resistance.

In the general formula (1), M is preferably a metal atom selected from the group consisting of Al, Ti, Zr, and Sn. Use of these metal atoms enables formation of a polymetalloxane having a high refractive index. More preferably, it is Ti or Zr.

In the general formula (1), m is preferably 3 or more and 5 or less.

The lower limit of the weight average molecular weight of the polymetalloxane is preferably 500 or more, more preferably 1,000 or more, and still more preferably 10,000 or more. The upper limit is preferably 1,000,000 or less, more preferably 500,000 or less, and still more preferably 200,000 or less. When the weight average molecular weight is in the above range, coating properties are improved. When the weight average molecular weight is the lower limit or more, physical properties of the cured film mentioned later are improved, thus obtaining a cured film particularly excellent in crack resistance.

The weight average molecular weight in the present invention means a value in terms of polystyrene measured by gel permeation chromatography (GPC).

The weight average molecular weight of the polymetalloxane can be determined, for example, by the following method. The polymetalloxane is dissolved in an eluent such that the concentration became 0.2% by weight to prepare a sample solution. Subsequently, the sample solution is poured into a column packed with a porous gel and an eluent. The column eluate is detected by a differential refractive index detector and the elution time is analyzed to determine the weight average molecular weight. N-methyl-2-pyrrolidone containing lithium-chloride dissolved therein is suitably used as the eluent.

(Method for Producing Polymetalloxane)

There is no particular limitation on the synthesis method of the polymetalloxane having the constituent unit represented by the general formula (1), and the synthesis method preferably includes the step of polycondensing a compound represented by the following general formula (2) or a hydrolysate thereof. Namely, the present invention is directed to, in another aspect, a method for producing a polymetalloxane, which including the step of polycondensing a compound represented by the following general formula (2).

[Chemical Formula 4]

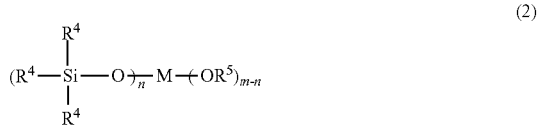

(2)

Wherein $R^4$ is optionally selected from a hydroxy group, an alkyl group having 1 to 12 carbon atoms, an alicyclic alkyl group having 5 to 12 carbon atoms, an alkoxy group having 1 to 12 carbon atoms, or an aromatic group having 6 to 30 carbon atoms. $R^5$ is optionally selected from a hydrogen atom or an alkyl group having 1 to 12 carbon atoms. When plural $R^4$ and $R^5$ exist, they may be the same or different. M represents a metal atom selected from the group consisting of Al, Ti, V, Cr, Mn, Fe, Co, Ni, Cu, Zn, Ga, Ge, Zr, Nb, Mo, Ru, Rh, Pd, Ag, In, Sn, Sb, Hf, Ta, W, Re, Os, Ir, Pt, Au, Tl, and Bi. m is an integer indicating a valence of a metal atom M, and n is an integer of 1 to (m−1), or a hydrolysate thereof.

More specifically, it is preferable to synthesize by optionally hydrolyzing the compound represented by the general formula (2), followed by partial condensation and polymerization. Here, the partial condensation means not to condense all the M-OH of the hydrolyzate, but to leave a part of M-OH in the resultant polymetalloxane. Under the general condensation conditions as mentioned later, generally, M-OH partially remains. The amount of remaining M-OH is not limited.

In general, when water is added to the metal alkoxide, the alkoxy group has high hydrolyzability, thus producing a metal hydroxide compound in which all the alkoxy groups in the molecule are hydrolyzed. This metal hydroxide compound aggregates in the solution and becomes insoluble in the solvent, and thus precipitation occurs.

Meanwhile, because of low hydrolyzability of the siloxy group represented by ($R^3_3SiO—$) in the compound represented by the general formula (2), it is possible to selectively hydrolyze the alkoxy group by addition of water. It is possible for the resulting hydrolyzate to obtain a transparent and homogeneous solution without aggregating in the solution due to the steric hindrance of the siloxy group. For this reason, it is possible to increase the degree of hydrolysis as compared with conventional technology. Therefore, it is possible to obtain a high molecular weight polymetalloxane, particularly a polymetalloxane having a weight average molecular weight exceeding 10,000, by hydrolyzing and polycondensing the compound represented by the general formula (2).

As specific examples of the compound represented by the general formula (2), for example, when the metal atom M is Ti, examples of those in which n=1 include:
trimethoxy(trimethylsiloxy)titanium,
triethoxy(trimethylsiloxy)titanium,
tripropoxy(trimethylsiloxy)titanium, triisopropoxy(trimethylsiloxy)titanium,
tributoxy(trimethylsiloxy)titanium,
triisobutoxy(trimethylsiloxy)titanium,
tri-s-butoxy(trimethylsiloxy)titanium,
tri-t-butoxy(trimethylsiloxy)titanium,
tricyclohexoxy(trimethylsiloxy)titanium,
triphenoxy(trimethylsiloxy)titanium;
trimethoxy(triethylsiloxy)titanium,
triethoxy(triethylsiloxy)titanium,
tripropoxy(triethylsiloxy)titanium,
triisopropoxy(triethylsiloxy)titanium,
tributoxy(triethylsiloxy)titanium,
triisobutoxy(triethylsiloxy)titanium,
tri-s-butoxy(triethylsiloxy)titanium,
tri-t-butoxy(triethylsiloxy)titanium,
tricyclohexoxy(triethylsiloxy)titanium,
triphenoxy(triethylsiloxy)titanium;
trimethoxy(tripropylsiloxy)titanium,
triethoxy(tripropylsiloxy)titanium,
tripropoxy(tripropylsiloxy)titanium,
triisopropoxy(tripropylsiloxy)titanium,
tributoxy(tripropylsiloxy)titanium,
triisobutoxy(tripropylsiloxy)titanium,
tri-s-butoxy(tripropylsiloxy)titanium,
tri-t-butoxy(tripropylsiloxy)titanium,
tricyclohexoxy(tripropylsiloxy)titanium,
triphenoxy(tripropylsiloxy)titanium;
trimethoxy(triisopropylsiloxy)titanium,
triethoxy(triisopropylsiloxy)titanium,
tripropoxy(triisopropylsiloxy)titanium,
triisopropoxy(triisopropylsiloxy)titanium,
tributoxy(triisopropylsiloxy)titanium,
triisobutoxy(triisopropylsiloxy)titanium,
tri-s-butoxy(triisopropylsiloxy)titanium,
tri-t-butoxy(triisopropylsiloxy)titanium,
tricyclohexoxy(triisopropylsiloxy)titanium,
triphenoxy(triisopropylsiloxy)titanium;
trimethoxy(tributylsiloxy)titanium,
triethoxy(tributylsiloxy)titanium,
tripropoxy(tributylsiloxy)titanium,
triisopropoxy(tributylsiloxy)titanium,
tributoxy(tributylsiloxy)titanium,
triisobutoxy(tributylsiloxy)titanium,
tri-s-butoxy(tributylsiloxy)titanium,
tri-t-butoxy(tributylsiloxy)titanium,
tricyclohexoxy(tributylsiloxy)titanium,
triphenoxy(tributylsiloxy)titanium;
trimethoxy(triisobutylsiloxy)titanium,
triethoxy(triisobutylsiloxy)titanium,
tripropoxy(triisobutylsiloxy)titanium,
triisopropoxy(triisobutylsiloxy)titanium,
tributoxy(triisobutylsiloxy)titanium,
triisobutoxy(triisobutylsiloxy)titanium,
tri-s-butoxy(triisobutylsiloxy)titanium,
tri-t-butoxy(triisobutylsiloxy)titanium,
tricyclohexoxy(triisobutylsiloxy)titanium,
triphenoxy(triisobutylsiloxy)titanium;
trimethoxy(tri-s-butoxysiloxy)titanium,
triethoxy(tri-s-butoxysiloxy)titanium,
tripropoxy(tri-s-butoxysiloxy)titanium,
triisopropoxy(tri-s-butoxysiloxy)titanium,
tributoxy(tri-s-butoxysiloxy)titanium,
triisobutoxy(tri-s-butoxysiloxy)titanium,
tri-s-butoxy(tri-s-butoxysiloxy)titanium,
tri-t-butoxy(tri-s-butoxysiloxy)titanium,
tricyclohexoxy(tri-s-butoxysiloxy)titanium,
triphenoxy(tri-s-butoxysiloxy)titanium;

trimethoxy(tri-t-butoxysiloxy)titanium,
triethoxy(tri-t-butoxysiloxy)titanium,
tripropoxy(tri-t-butoxysiloxy)titanium,
triisopropoxy(tri-t-butoxysiloxy)titanium,
tributoxy(tri-t-butoxysiloxy)titanium,
triisobutoxy(tri-t-butoxysiloxy)titanium,
tri-s-butoxy(tri-t-butoxysiloxy)titanium,
tri-t-butoxy(tri-t-butoxysiloxy)titanium,
tricyclohexoxy(tri-t-butoxysiloxy)titanium,
triphepoxy(tri-t-butoxysiloxy)titanium;
trimethoxy(tricyclohexylsiloxy)titanium,
triethoxy(tricyclohexylsiloxy)titanium,
tripropoxy(tricyclohexylsiloxy)titanium,
triisopropoxy(tricyclohexylsiloxy)titanium,
tributoxy(tricyclohexylsiloxy)titanium,
triisobutoxy(tricyclohexylsiloxy)titanium,
tri-s-butoxy(tricyclohexylsiloxy)titanium,
tri-t-butoxy(tricyclohexylsiloxy)titanium,
tricyclohexoxy(tricyclohexylsiloxy)titanium,
triphenoxy(tricyclohexylsiloxy)titanium;
trimethoxy(triphenylsiloxy)titanium,
triethoxy(triphenylsiloxy)titanium,
tripropoxy(triphenylsiloxy)titanium,
triisopropoxy(triphenylsiloxy)titanium,
tributoxy(triphenylsiloxy)titanium,
triisobutoxy(triphenylsiloxy)titanium,
tri-s-butoxy(triphenylsiloxy)titanium,
tri-t-butoxy(triphenylsiloxy)titanium,
tricyclohexoxy(triphenylsiloxy)titanium,
triphenoxy(triphenylsiloxy)titanium, and the like; and examples of those in which n=2 include:
dimethoxybis(trimethylsiloxy)titanium,
diethoxybis(trimethylsiloxy)titanium,
dipropoxybis(trimethylsiloxy)titanium,
diisopropoxybis(trimethylsiloxy)titanium,
dibutoxybis(trimethylsiloxy)titanium,
diisobutoxybis(trimethylsiloxy)titanium,
di-s-butoxybis(trimethylsiloxy)titanium,
di-t-butoxybis(trimethylsiloxy)titanium,
dicyclohexoxybis(trimethylsiloxy)titanium,
diphenoxybis(trimethylsiloxy)titanium;
dimethoxybis(triethylsiloxy)titanium,
diethoxybis(triethylsiloxy)titanium,
dipropoxybis(triethylsiloxy)titanium,
diisopropoxybis(triethylsiloxy)titanium,
dibutoxybis(triethylsiloxy)titanium,
diisobutoxybis(triethylsiloxy)titanium,
di-s-butoxybis(triethylsiloxy)titanium,
di-t-butoxybis(triethylsiloxy)titanium,
dicyclohexoxybis(triethylsiloxy)titanium,
diphenoxybis(triethylsiloxy)titanium;
dimethoxybis(tripropylsiloxy)titanium,
diethoxybis(tripropylsiloxy)titanium,
dipropoxybis(tripropylsiloxy)titanium,
diisopropoxybis(tripropylsiloxy)titanium,
dibutoxybis(tripropylsiloxy)titanium,
diisobutoxybis(tripropylsiloxy)titanium,
di-s-butoxybis(tripropylsiloxy)titanium,
di-t-butoxybis(tripropylsiloxy)titanium,
dicyclohexoxybis(tripropylsiloxy)titanium,
diphenoxybis(tripropylsiloxy)titanium;
dimethoxybis(triisopropylsiloxy)titanium,
diethoxybis(triisopropylsiloxy)titanium,
dipropoxybis(triisopropylsiloxy)titanium,
diisopropoxybis(triisopropylsiloxy)titanium,
dibutoxybis(triisopropylsiloxy)titanium,
diisobutoxybis(triisopropylsiloxy)titanium, di-s-butoxybis(triisopropylsiloxy)titanium,
di-t-butoxybis(triisopropylsiloxy)titanium,
dicyclohexoxybis(triisopropylsiloxy)titanium,
diphenoxybis(triisopropylsiloxy)titanium;
dimethoxybis(tributylsiloxy)titanium,
diethoxybis(tributylsiloxy)titanium,
dipropoxybis(tributylsiloxy)titanium,
diisopropoxybis(tributylsiloxy)titanium,
dibutoxybis(tributylsiloxy)titanium,
diisobutoxybis(tributylsiloxy)titanium,
di-s-butoxybis(tributylsiloxy)titanium,
di-t-butoxybis(tributylsiloxy)titanium,
dicyclohexoxybis(tributylsiloxy)titanium,
diphenoxybis(tributylsiloxy)titanium;
dimethoxybis(triisobutylsiloxy)titanium,
diethoxybis(triisobutylsiloxy)titanium,
dipropoxybis(triisobutylsiloxy)titanium,
diisopropoxybis(triisobutylsiloxy)titanium,
dibutoxybis(triisobutylsiloxy)titanium,
diisobutoxybis(triisobutylsiloxy)titanium,
di-s-butoxybis(triisobutylsiloxy)titanium,
di-t-butoxybis(triisobutylsiloxy)titanium,
dicyclohexoxybis(triisobutylsiloxy)titanium,
diphenoxybis(triisobutylsiloxy)titanium;
dimethoxybis(tri-s-butoxysiloxy)titanium,
diethoxybis(tri-s-butoxysiloxy)titanium,
dipropoxybis(tri-s-butoxysiloxy)titanium,
diisopropoxybis(tri-s-butoxysiloxy)titanium,
dibutoxybis(tri-s-butoxysiloxy)titanium,
diisobutoxybis(tri-s-butoxysiloxy)titanium,
di-s-butoxybis(tri-s-butoxysiloxy)titanium,
di-t-butoxybis(tri-s-butoxysiloxy)titanium,
dicyclohexoxybis(tri-s-butoxysiloxy)titanium,
diphenoxybis(tri-s-butoxysiloxy)titanium;
dimethoxybis(tri-t-butoxysiloxy)titanium,
diethoxybis(tri-t-butoxysiloxy)titanium,
dipropoxybis(tri-t-butoxysiloxy)titanium,
diisopropoxybis(tri-t-butoxysiloxy)titanium,
dibutoxybis(tri-t-butoxysiloxy)titanium,
diisobutoxybis(tri-t-butoxysiloxy)titanium,
di-s-butoxybis(tri-t-butoxysiloxy)titanium,
di-t-butoxybis(tri-t-butoxysiloxy)titanium,
dicyclohexoxybis(tri-t-butoxysiloxy)titanium,
diphenoxybis(tri-t-butoxysiloxy)titanium;
dimethoxybis(tricyclohexylsiloxy)titanium,
diethoxybis(tricyclohexylsiloxy)titanium,
dipropoxybis(tricyclohexylsiloxy)titanium,
diisopropoxybis(tricyclohexylsiloxy)titanium,
dibutoxybis(tricyclohexylsiloxy)titanium,
diisobutoxybis(tricyclohexylsiloxy)titanium,
di-s-butoxybis(tricyclohexylsiloxy)titanium,
di-t-butoxybis(tricyclohexylsiloxy)titanium,
dicyclohexoxybis(tricyclohexylsiloxy)titanium,
diphenoxybis(tricyclohexylsiloxy)titanium;
dimethoxybis(triphenylsiloxy)titanium,
diethoxybis(triphenylsiloxy)titanium,
dipropoxybis(triphenylsiloxy)titanium,
diisopropoxybis(triphenylsiloxy)titanium,
dibutoxybis(triphenylsiloxy)titanium,
diisobutoxybis(triphenylsiloxy)titanium,
di-s-butoxybis(triphenylsiloxy)titanium,
di-t-butoxybis(triphenylsiloxy)titanium,
dicyclohexoxybis(triphenylsiloxy)titanium,
diphenoxybis(triphenylsiloxy)titanium, and the like.

When the metal atom M is Zr, examples of those in which n=1 include:
trimethoxy(trimethylsiloxy)zirconium,
triethoxy(trimethylsiloxy)zirconium,
tripropoxy(trimethylsiloxy)zirconium,
triisopropoxy(trimethylsiloxy)zirconium,
tributoxy(trimethylsiloxy)zirconium,
triisobutoxy(trimethylsiloxy)zirconium,
tri-s-butoxy(trimethylsiloxy)zirconium,
tri-t-butoxy(trimethylsiloxy)zirconium,
tricyclohexoxy(trimethylsiloxy)zirconium,
triphenoxy(trimethylsiloxy)zirconium;
trimethoxy(triethylsiloxy)zirconium,
triethoxy(triethylsiloxy)zirconium,
tripropoxy(triethylsiloxy)zirconium,
triisopropoxy(triethylsiloxy)zirconium,
tributoxy(triethylsiloxy)zirconium,
triisobutoxy(triethylsiloxy)zirconium,
tri-s-butoxy(triethylsiloxy)zirconium,
tri-t-butoxy(triethylsiloxy)zirconium,
tricyclohexoxy(triethylsiloxy)zirconium,
triphenoxy(triethylsiloxy)zirconium;
trimethoxy(tripropylsiloxy)zirconium,
triethoxy(tripropylsiloxy)zirconium,
tripropoxy(tripropylsiloxy)zirconium,
triisopropoxy(tripropylsiloxy)zirconium,
tributoxy(tripropylsiloxy)zirconium,
triisobutoxy(tripropylsiloxy)zirconium,
tri-s-butoxy(tripropylsiloxy)zirconium,
tri-t-butoxy(tripropylsiloxy)zirconium,
tricyclohexoxy(tripropylsiloxy)zirconium,
triphenoxy(tripropylsiloxy)zirconium;
trimethoxy(triisopropylsiloxy)zirconium,
triethoxy(triisopropylsiloxy)zirconium,
tripropoxy(triisopropylsiloxy)zirconium,
triisopropoxy(triisopropylsiloxy)zirconium,
tributoxy(triisopropylsiloxy)zirconium,
triisobutoxy(triisopropylsiloxy)zirconium,
tri-s-butoxy(triisopropylsiloxy)zirconium,
tri-t-butoxy(triisopropylsiloxy)zirconium,
tricyclohexoxy(triisopropylsiloxy)zirconium,
triphenoxy(triisopropylsiloxy)zirconium;
trimethoxy(tributylsiloxy)zirconium,
triethoxy(tributylsiloxy)zirconium,
tripropoxy(tributylsiloxy)zirconium,
triisopropoxy(tributylsiloxy)zirconium,
tributoxy(tributylsiloxy)zirconium,
triisobutoxy(tributylsiloxy)zirconium,
tri-s-butoxy(tributylsiloxy)zirconium,
tri-t-butoxy(tributylsiloxy)zirconium,
tricyclohexoxy(tributylsiloxy)zirconium,
triphenoxy(tributylsiloxy)zirconium;
trimethoxy(triisobutylsiloxy)zirconium,
triethoxy(triisobutylsiloxy)zirconium,
tripropoxy(triisobutylsiloxy)zirconium,
triisopropoxy(triisobutylsiloxy)zirconium,
tributoxy(triisobutylsiloxy)zirconium,
triisobutoxy(triisobutylsiloxy)zirconium,
tri-s-butoxy(triisobutylsiloxy)zirconium,
tri-t-butoxy(triisobutylsiloxy)zirconium,
tricyclohexoxy(triisobutylsiloxy)zirconium,
triphenoxy(triisobutylsiloxy)zirconium;
trimethoxy(tri-s-butoxysiloxy)zirconium,
triethoxy(tri-s-butoxysiloxy)zirconium,
tripropoxy(tri-s-butoxysiloxy)zirconium,
triisopropoxy(tri-s-butoxysiloxy)zirconium,
tri-n-butoxy(tri-s-butoxysiloxy)zirconium, triisobutoxy(tri-s-butoxysiloxy)zirconium,
tri-s-butoxy(tri-s-butoxysiloxy)zirconium,
tri-t-butoxy(tri-s-butoxysiloxy)zirconium,
tricyclohexoxy(tri-s-butoxysiloxy)zirconium,
triphenoxy(tri-s-butoxysiloxy)zirconium;
trimethoxy(tri-t-butoxysiloxy)zirconium,
triethoxy(tri-t-butoxysiloxy)zirconium,
tripropoxy(tri-t-butoxysiloxy)zirconium,
triisopropoxy(tri-t-butoxysiloxy)zirconium,
tri-n-butoxy(tri-t-butoxysiloxy)zirconium,
triisobutoxy(tri-t-butoxysiloxy)zirconium,
tri-s-butoxy(tri-t-butoxysiloxy)zirconium,
tri-t-butoxy(tri-t-butoxysiloxy)zirconium,
tricyclohexoxy(tri-t-butoxysiloxy)zirconium,
triphenoxy(tri-t-butoxysiloxy)zirconium;
trimethoxy(tricyclohexylsiloxy)zirconium,
triethoxy(tricyclohexylsiloxy)zirconium,
tripropoxy(tricyclohexylsiloxy)zirconium,
triisopropoxy(tricyclohexylsiloxy)zirconium,
tributoxy(tricyclohexylsiloxy)zirconium,
triisobutoxy(tricyclohexylsiloxy)zirconium,
tri-s-butoxy(tricyclohexylsiloxy)zirconium,
tri-t-butoxy(tricyclohexylsiloxy)zirconium,
tricyclohexoxy(tricyclohexylsiloxy)zirconium,
triphenoxy(tricyclohexylsiloxy)zirconium;
trimethoxy(triphenylsiloxy)zirconium,
triethoxy(triphenylsiloxy)zirconium,
tripropoxy(triphenylsiloxy)zirconium,
triisopropoxy(triphenylsiloxy)zirconium,
tributoxy(triphenylsiloxy)zirconium,
triisobutoxy(triphenylsiloxy)zirconium,
tri-s-butoxy(triphenylsiloxy)zirconium,
tri-t-butoxy(triphenylsiloxy)zirconium,
tricyclohexoxy(triphenylsiloxy)zirconium,
triphenoxy(triphenylsiloxy)zirconium, and the like; and examples of those in which n=2 include:
dimethoxybis(trimethylsiloxy)zirconium,
diethoxybis(trimethylsiloxy)zirconium,
dipropoxybis(trimethylsiloxy)zirconium,
diisopropoxybis(trimethylsiloxy)zirconium,
dibutoxybis(trimethylsiloxy)zirconium,
diisobutoxybis(trimethylsiloxy)zirconium,
di-s-butoxybis(trimethylsiloxy)zirconium,
di-t-butoxybis(trimethylsiloxy)zirconium,
dicyclohexoxybis(trimethylsiloxy)zirconium,
diphenoxybis(trimethylsiloxy)zirconium;
dimethoxybis(triethylsiloxy)zirconium,
diethoxybis(triethylsiloxy)zirconium,
dipropoxybis(triethylsiloxy)zirconium,
diisopropoxybis(triethylsiloxy)zirconium,
dibutoxybis(triethylsiloxy)zirconium,
diisobutoxybis(triethylsiloxy)zirconium,
di-s-butoxybis(triethylsiloxy)zirconium,
di-t-butoxybis(triethylsiloxy)zirconium,
dicyclohexoxybis(triethylsiloxy)zirconium,
diphenoxybis(triethylsiloxy)zirconium;
dimethoxybis(tripropylsiloxy)zirconium,
diethoxybis(tripropylsiloxy)zirconium,
dipropoxybis(tripropylsiloxy)zirconium,
diisopropoxybis(tripropylsiloxy)zirconium,
dibutoxybis(tripropylsiloxy)zirconium,
diisobutoxybis(tripropylsiloxy)zirconium,
di-s-butoxybis(tripropylsiloxy)zirconium,
di-t-butoxybis(tripropylsiloxy)zirconium,
dicyclohexoxybis(tripropylsiloxy)zirconium,
diphenoxybis(tripropylsiloxy)zirconium;
dimethoxybis(triisopropylsiloxy)zirconium,
diethoxybis(triisopropylsiloxy)zirconium,
dipropoxybis(triisopropylsiloxy)zirconium,
diisopropoxybis(triisopropylsiloxy)zirconium,
dibutoxybis(triisopropylsiloxy)zirconium,
diisobutoxybis(triisopropylsiloxy)zirconium,
di-s-butoxybis(triisopropylsiloxy)zirconium,
di-t-butoxybis(triisopropylsiloxy)zirconium,
dicyclohexoxybis(triisopropylsiloxy)zirconium,
diphenoxybis(triisopropylsiloxy)zirconium;
dimethoxybis(tributylsiloxy)zirconium,
diethoxybis(tributylsiloxy)zirconium,
dipropoxybis(tributylsiloxy)zirconium,
diisopropoxybis(tributylsiloxy)zirconium,
dibutoxybis(tributylsiloxy)zirconium,
diisobutoxybis(tributylsiloxy)zirconium,
di-s-butoxybis(tributylsiloxy)zirconium,
di-t-butoxybis(tributylsiloxy)zirconium,
dicyclohexoxybis(tributylsiloxy)zirconium,
diphenoxybis(tributylsiloxy)zirconium;
dimethoxybis(triisobutylsiloxy)zirconium,
diethoxybis(triisobutylsiloxy)zirconium,
dipropoxybis(triisobutylsiloxy)zirconium,
diisopropoxybis(triisobutylsiloxy)zirconium,
dibutoxybis(triisobutylsiloxy)zirconium,
diisobutoxybis(triisobutylsiloxy)zirconium,
di-s-butoxybis(triisobutylsiloxy)zirconium,
di-t-butoxybis(triisobutylsiloxy)zirconium,
dicyclohexoxybis(triisobutylsiloxy)zirconium,
diphenoxybis(triisobutylsiloxy)zirconium;
dimethoxybis(tri-s-butoxysiloxy)zirconium,
diethoxybis(tri-s-butoxysiloxy)zirconium,
dipropoxybis(tri-s-butoxysiloxy)zirconium,
diisopropoxybis(tri-s-butoxysiloxy)zirconium,
dibutoxybis(tri-s-butoxysiloxy)zirconium,
diisobutoxybis(tri-s-butoxysiloxy)zirconium,
di-s-butoxybis(tri-s-butoxysiloxy)zirconium,
di-t-butoxybis(tri-s-butoxysiloxy)zirconium,
dicyclohexoxybis(tri-s-butoxysiloxy)zirconium,
diphenoxybis(tri-s-butoxysiloxy)zirconium;
dimethoxybis(tri-t-butoxysiloxy)zirconium,
diethoxybis(tri-t-butoxysiloxy)zirconium,
dipropoxybis(tri-t-butoxysiloxy)zirconium,
diisopropoxybis(tri-t-butoxysiloxy)zirconium,
dibutoxybis(tri-t-butoxysiloxy)zirconium,
diisobutoxybis(tri-t-butoxysiloxy)zirconium,
di-s-butoxybis(tri-t-butoxysiloxy)zirconium,
di-t-butoxybis(tri-t-butoxysiloxy)zirconium,
dicyclohexoxybis(tri-t-butoxysiloxy)zirconium,
diphenoxybis(tri-t-butoxysiloxy)zirconium;
dimethoxybis(tricyclohexylsiloxy)zirconium,
diethoxybis(tricyclohexylsiloxy)zirconium,
dipropoxybis(tricyclohexylsiloxy)zirconium,
diisopropoxybis(tricyclohexylsiloxy)zirconium,
di-n-butoxybis(tricyclohexylsiloxy)zirconium,
diisobutoxybis(tricyclohexylsiloxy)zirconium,
di-s-butoxybis(tricyclohexylsiloxy)zirconium,
di-t-butoxybis(tricyclohexylsiloxy)zirconium,
dicyclohexoxybis(tricyclohexylsiloxy)zirconium,
diphenoxybis(tricyclohexylsiloxy)zirconium;
dimethoxybis(triphenylsiloxy)zirconium,
diethoxybis(triphenylsiloxy)zirconium,
dipropoxybis(triphenylsiloxy)zirconium,
diisopropoxybis(triphenylsiloxy)zirconium,
dibutoxybis(triphenylsiloxy)zirconium,
diisobutoxybis(triphenylsiloxy)zirconium,
di-s-butoxybis(triphenylsiloxy)zirconium,
di-t-butoxybis(triphenylsiloxy)zirconium,
dicyclohexoxybis(triphenylsiloxy)zirconium,
diphenoxybis(triphenylsiloxy)zirconium, and the like.

It is particularly preferred to include, in the method for synthesizing a polymetalloxane having a constituent unit represented by the general formula (1), the step of optionally hydrolyzing and polycondensing a compound in which at least one of $R^5$ in the general formula (2) is a hydrogen atom. That is, the compound represented by the general formula (2) is preferably a compound represented by the following general formula (3).

[Chemical Formula 5]

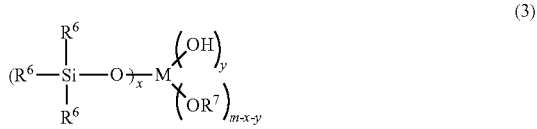

(3)

$R^6$ is the same as $R^4$ in the general formula (1), $R^7$ is an alkyl group having 1 to 12 carbon atoms. m is an integer indicating a valence of a metal atom M, x is an integer of 1 to (m−1), y is an integer of 1 to (m−1), and x+y≤m.

It is preferable that y is an integer of 2 to (m−1).

In general, a compound having a hydroxy group is aggregated by a hydrogen bond of a hydroxy group and becomes insoluble in an organic solvent. However, since the metal compound represented by the general formula (3) has a siloxy group, it is possible to obtain a transparent and uniform solution without aggregating in an organic solvent due to the steric hindrance of the siloxy group. Since the hydroxy group can cause dehydration condensation, it is possible to obtain a high molecular weight polymetalloxane by polycondensing the metal compound represented by the general formula (3). Because of high heat resistance of the siloxy group, it is possible to obtain a high molecular weight polymetalloxane excellent in transparency.

When $OR^7$ exists, hydrolysis is preferably performed prior to polycondensation. As is likewise the case of the compound represented by the general formula (2), the hydrolyzate of the compound represented by the general formula (3) can give a transparent and uniform solution without causing aggregation in the solution due to the steric hindrance of the siloxy group. Therefore, it is possible to increase the degree of hydrolysis as compared with conventional technology.

As the metal compound represented by the general formula (3), for example, when the metal atom M is Ti, examples of those in which y=2 include:
methoxydihydroxy(trimethylsiloxy)titanium,
ethoxydihydroxy(trimethylsiloxy)titanium,
propoxydihydroxy(trimethylsiloxy)titanium,
isopropoxydihydroxy(trimethylsiloxy)titanium,
butoxydihydroxy(trimethylsiloxy)titanium,
isobutoxydihydroxy(trimethylsiloxy)titanium,
s-butoxydihydroxy(trimethylsiloxy)titanium,
t-butoxydihydroxy(trimethylsiloxy)titanium,
cyclohexoxydihydroxy(trimethylsiloxy)titanium,
phenoxydihydroxy(trimethylsiloxy)titanium;
methoxydihydroxy(triethylsiloxy)titanium,
ethoxydihydroxy(triethylsiloxy)titanium,
propoxydihydroxy(triethylsiloxy)titanium,
isopropoxydihydroxy(triethylsiloxy)titanium,
butoxydihydroxy(triethylsiloxy)titanium,
isobutoxydihydroxy(triethylsiloxy)titanium,
s-butoxydihydroxy(triethylsiloxy)titanium,
t-butoxydihydroxy(triethylsiloxy)titanium,
cyclohexoxydihydroxy(triethylsiloxy)titanium,
phenoxydihydroxy(triethylsiloxy)titanium;
methoxydihydroxy(tripropylsiloxy)titanium,
ethoxydihydroxy(tripropylsiloxy)titanium,
propoxydihydroxy(tripropylsiloxy)titanium,
isopropoxydihydroxy(tripropylsiloxy)titanium,
butoxydihydroxy(tripropylsiloxy)titanium,
isobutoxydihydroxy(tripropylsiloxy)titanium,
s-butoxydihydroxy(tripropylsiloxy)titanium,
t-butoxydihydroxy(tripropylsiloxy)titanium,
cyclohexoxydihydroxy(tripropylsiloxy)titanium,
phenoxydihydroxy(tripropylsiloxy)titanium;
methoxydihydroxy(triisopropylsiloxy)titanium,
ethoxydihydroxy(triisopropylsiloxy)titanium,
propoxydihydroxy(triisopropylsiloxy)titanium,
isopropoxydihydroxy(triisopropylsiloxy)titanium,
butoxydihydroxy(triisopropylsiloxy)titanium,
isobutoxydihydroxy(triisopropylsiloxy)titanium,
s-butoxydihydroxy(triisopropylsiloxy)titanium,
t-butoxydihydroxy(triisopropylsiloxy)titanium,
cyclohexoxydihydroxy(triisopropylsiloxy)titanium,
phenoxydihydroxy(triisopropylsiloxy)titanium;
methoxydihydroxy(tributylsiloxy)titanium,
ethoxydihydroxy(tributylsiloxy)titanium,
propoxydihydroxy(tributylsiloxy)titanium,
isopropoxydihydroxy(tributylsiloxy)titanium,
butoxydihydroxy(tributylsiloxy)titanium,
isobutoxydihydroxy(tributylsiloxy)titanium,
butoxydihydroxy(tributylsiloxy)titanium,
t-butoxydihydroxy(tributylsiloxy)titanium,
cyclohexoxydihydroxy(tributylsiloxy)titanium,
phenoxydihydroxy(tributylsiloxy)titanium;
methoxydihydroxy(triisobutylsiloxy)titanium,
ethoxydihydroxy(triisobutylsiloxy)titanium,
propoxydihydroxy(triisobutylsiloxy)titanium,
isopropoxydihydroxy(triisobutylsiloxy)titanium,
butoxydihydroxy(triisobutylsiloxy)titanium,
isobutoxydihydroxy(triisobutylsiloxy)titanium,
s-butoxydihydroxy(triisobutylsiloxy)titanium,
t-butoxydihydroxy(triisobutylsiloxy)titanium,
cyclohexoxydihydroxy(triisobutylsiloxy)titanium,
phenoxydihydroxy(triisobutylsiloxy)titanium;
methoxydihydroxy(tri-s-butoxysiloxy)titanium,
ethoxydihydroxy(tri-s-butoxysiloxy)titanium,
propoxydihydroxy(tri-s-butoxysiloxy)titanium,
isopropoxydihydroxy(tri-s-butoxysiloxy)titanium,
butoxydihydroxy(tri-s-butoxysiloxy)titanium,
isobutoxydihydroxy(tri-s-butoxysiloxy)titanium,
s-butoxydihydroxy(tri-s-butoxysiloxy)titanium,
t-butoxydihydroxy(tri-s-butoxysiloxy)titanium,
cyclohexoxydihydroxy(tri-s-butoxysiloxy)titanium,
phenoxydihydroxy(tri-s-butoxysiloxy)titanium;
methoxydihydroxy(tri-t-butoxysiloxy)titanium,
ethoxydihydroxy(tri-t-butoxysiloxy)titanium,
propoxydihydroxy(tri-t-butoxysiloxy)titanium,
isopropoxydihydroxy(tri-t-butoxysiloxy)titanium,
butoxydihydroxy(tri-t-butoxysiloxy)titanium,
isobutoxydihydroxy(tri-t-butoxysiloxy)titanium,
s-butoxydihydroxy(tri-t-butoxysiloxy)titanium,
t-butoxydihydroxy(tri-t-butoxysiloxy)titanium,
cyclohexoxydihydroxy(tri-t-butoxysiloxy)titanium,
phenoxydihydroxy(tri-t-butoxysiloxy)titanium;
methoxydihydroxy(tricyclohexylsiloxy)titanium,
ethoxydihydroxy(tricyclohexylsiloxy)titanium,
propoxydihydroxy(tricyclohexylsiloxy)titanium,
isopropoxydihydroxy(tricyclohexylsiloxy)titanium,
butoxydihydroxy(tricyclohexylsiloxy)titanium,
isobutoxydihydroxy(tricyclohexylsiloxy)titanium, s-butoxydihydroxy(tricyclohexylsiloxy)titanium,
t-butoxydihydroxy(tricyclohexylsiloxy)titanium,
cyclohexoxydihydroxy(tricyclohexylsiloxy)titanium,
phenoxydihydroxy(tricyclohexylsiloxy)titanium;
methoxydihydroxy(triphenylsiloxy)titanium,
ethoxydihydroxy(triphenylsiloxy)titanium,
propoxydihydroxy(triphenylsiloxy)titanium,
isopropoxydihydroxy(triphenylsiloxy)titanium,
butoxydihydroxy(triphenylsiloxy)titanium,
isobutoxydihydroxy(triphenylsiloxy)titanium,
s-butoxydihydroxy(triphenylsiloxy)titanium,
t-butoxydihydroxy(triphenylsiloxy)titanium,
cyclohexoxydihydroxy(triphenylsiloxy)titanium,
phenoxydihydroxy(triphenylsiloxy)titanium, and the like; and examples of those in which y=3 include:
trihydroxy(trimethylsiloxy)titanium,
trihydroxy(triethylsiloxy)titanium,
trihydroxy(tripropylsiloxy)titanium,
trihydroxy(triisopropylsiloxy)titanium,
trihydroxy(tributylsiloxy)titanium,
trihydroxy(triisobutylsiloxy)titanium,
trihydroxy(tri-s-butoxysiloxy)titanium,
trihydroxy(tri-t-butoxysiloxy)titanium,
trihydroxy(tricyclohexylsiloxy)titanium,
trihydroxy(triphenylsiloxy)titanium, and the like.

When the metal atom M is Zr, examples of those in which y=2 include:
methoxydihydroxy(trimethylsiloxy)zirconium,
ethoxydihydroxy(trimethylsiloxy)zirconium,
propoxydihydroxy(trimethylsiloxy)zirconium,
isopropoxydihydroxy(trimethylsiloxy)zirconium,
butoxydihydroxy(trimethylsiloxy)zirconium,
isobutoxydihydroxy(trimethylsiloxy)zirconium,
s-butoxydihydroxy(trimethylsiloxy)zirconium,
t-butoxydihydroxy(trimethylsiloxy)zirconium,
cyclohexoxydihydroxy(trimethylsiloxy)zirconium,
phenoxydihydroxy(trimethylsiloxy)zirconium;
methoxydihydroxy(triethylsiloxy)zirconium,
ethoxydihydroxy(triethylsiloxy)zirconium,
propoxydihydroxy(triethylsiloxy)zirconium,
isopropoxydihydroxy(triethylsiloxy)zirconium,
butoxydihydroxy(triethylsiloxy)zirconium,
isobutoxydihydroxy(triethylsiloxy)zirconium,
s-butoxydihydroxy(triethylsiloxy)zirconium,
t-butoxydihydroxy(triethylsiloxy)zirconium,
cyclohexoxydihydroxy(triethylsiloxy)zirconium,
phenoxydihydroxy(triethylsiloxy)zirconium;
methoxydihydroxy(tripropylsiloxy)zirconium,
ethoxydihydroxy(tripropylsiloxy)zirconium,
propoxydihydroxy(tripropylsiloxy)zirconium,
isopropoxydihydroxy(tripropylsiloxy)zirconium,
butoxydihydroxy(tripropylsiloxy)zirconium,
isobutoxydihydroxy(tripropylsiloxy)zirconium,
s-butoxydihydroxy(tripropylsiloxy)zirconium,
t-butoxydihydroxy(tripropylsiloxy)zirconium,
cyclohexoxydihydroxy(tripropylsiloxy)zirconium,
phenoxydihydroxy(tripropylsiloxy)zirconium;
methoxydihydroxy(triisopropylsiloxy)zirconium,
ethoxydihydroxy(triisopropylsiloxy)zirconium,
propoxydihydroxy(triisopropylsiloxy)zirconium,
isopropoxydihydroxy(triisopropylsiloxy)zirconium,
butoxydihydroxy(triisopropylsiloxy)zirconium,
isobutoxydihydroxy(triisopropylsiloxy)zirconium,
s-butoxydihydroxy(triisopropylsiloxy)zirconium,
t-butoxydihydroxy(triisopropylsiloxy)zirconium,
cyclohexoxydihydroxy(triisopropylsiloxy)zirconium,
phenoxydihydroxy(triisopropylsiloxy)zirconium;
methoxydihydroxy(tributylsiloxy)zirconium,
ethoxydihydroxy(tributylsiloxy)zirconium,
propoxydihydroxy(tributylsiloxy)zirconium,
isopropoxydihydroxy(tributylsiloxy)zirconium,
butoxydihydroxy(tributylsiloxy)zirconium,
isobutoxydihydroxy(tributylsiloxy)zirconium,
butoxydihydroxy(tributylsiloxy)zirconium,
t-butoxydihydroxy(tributylsiloxy)zirconium,
cyclohexoxydihydroxy(tributylsiloxy)zirconium,
phenoxydihydroxy(tributylsiloxy)zirconium;
methoxydihydroxy(triisobutylsiloxy)zirconium,
ethoxydihydroxy(triisobutylsiloxy)zirconium,
propoxydihydroxy(triisobutylsiloxy)zirconium,
isopropoxydihydroxy(triisobutylsiloxy)zirconium,
butoxydihydroxy(triisobutylsiloxy)zirconium,
isobutoxydihydroxy(triisobutylsiloxy)zirconium,
s-butoxydihydroxy(triisobutylsiloxy)zirconium,
t-butoxydihydroxy(triisobutylsiloxy)zirconium,
cyclohexoxydihydroxy(triisobutylsiloxy)zirconium,
phenoxydihydroxy(triisobutylsiloxy)zirconium;
methoxydihydroxy(tri-s-butoxysiloxy)zirconium,
ethoxydihydroxy(tri-s-butoxysiloxy)zirconium,
propoxydihydroxy(tri-s-butoxysiloxy)zirconium,
isopropoxydihydroxy(tri-s-butoxysiloxy)zirconium,
butoxydihydroxy(tri-s-butoxysiloxy)zirconium,
isobutoxydihydroxy(tri-s-butoxysiloxy)zirconium,
s-butoxydihydroxy(tri-s-butoxysiloxy)zirconium,
t-butoxydihydroxy(tri-s-butoxysiloxy)zirconium,
cyclohexoxydihydroxy(tri-s-butoxysiloxy)zirconium,
phenoxydihydroxy(tri-s-butoxysiloxy)zirconium;
methoxydihydroxy(tri-t-butoxysiloxy)zirconium,
ethoxydihydroxy(tri-t-butoxysiloxy)zirconium,
propoxydihydroxy(tri-t-butoxysiloxy)zirconium,
isopropoxydihydroxy(tri-t-butoxysiloxy)zirconium,
butoxydihydroxy(tri-t-butoxysiloxy)zirconium,
isobutoxydihydroxy(tri-t-butoxysiloxy)zirconium,
s-butoxydihydroxy(tri-t-butoxysiloxy)zirconium,
t-butoxydihydroxy(tri-t-butoxysiloxy)zirconium,
cyclohexoxydihydroxy(tri-t-butoxysiloxy)zirconium,
phenoxydihydroxy(tri-t-butoxysiloxy)zirconium;
methoxydihydroxy(tricyclohexylsiloxy)zirconium,
ethoxydihydroxy(tricyclohexylsiloxy)zirconium,
propoxydihydroxy(tricyclohexylsiloxy)zirconium,
isopropoxydihydroxy(tricyclohexylsiloxy)zirconium,
butoxydihydroxy(tricyclohexylsiloxy)zirconium,
isobutoxydihydroxy(tricyclohexylsiloxy)zirconium,
s-butoxydihydroxy(tricyclohexylsiloxy)zirconium,
t-butoxydihydroxy(tricyclohexylsiloxy)zirconium,
cyclohexoxydihydroxy(tricyclohexylsiloxy)zirconium,
phenoxydihydroxy(tricyclohexylsiloxy)zirconium;
methoxydihydroxy(triphenylsiloxy)zirconium,
ethoxydihydroxy(triphenylsiloxy)zirconium,
propoxydihydroxy(triphenylsiloxy)zirconium,
isopropoxydihydroxy(triphenylsiloxy)zirconium,
butoxydihydroxy(triphenylsiloxy)zirconium,
isobutoxydihydroxy(triphenylsiloxy)zirconium,
s-butoxydihydroxy(triphenylsiloxy)zirconium,
t-butoxydihydroxy(triphenylsiloxy)zirconium,
cyclohexoxydihydroxy(triphenylsiloxy)zirconium,
phenoxydihydroxy(triphenylsiloxy)zirconium, and the like; and
examples of those in which y=3 include:
trihydroxy(trimethylsiloxy)zirconium,
trihydroxy(triethylsiloxy)zirconium,
trihydroxy(tripropylsiloxy)zirconium,
trihydroxy(triisopropylsiloxy)zirconium,
trihydroxy(tributylsiloxy)zirconium, trihydroxy(triisobutylsiloxy)zirconium, trihydroxy(tri-s-butoxysiloxy)zirconium, trihydroxy(tri-t-butoxysiloxy)zirconium, trihydroxy(tricyclohexylsiloxy)zirconium, trihydroxy(triphenylsiloxy)zirconium, and the like.

(Method for Producing Compound Represented by General Formula (2))

There is no particular limitation on the method for producing the compound represented by the general formula (2). For example, when $R^5$ is an alkyl group having 1 to 12 carbon atoms, the compound can be obtained by reacting a metal alkoxide with a compound represented by the following general formula (4) at a predetermined molar ratio so as to obtain a compound in which n is 1, 2, or 3.

[Chemical Formula 6]

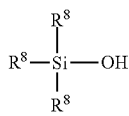

(4)

In the general formula (4), $R^8$ is the same as $R^4$ in the general formula (2).

Specific examples of the compound represented by the general formula (4) include trimethylsilanol, triethylsilanol, tripropylsilanol, triisopropylsilanol, tributylsilanol, triisobutylsilanol, tri-s-butylsilanol, tri-t-butylsilanol, tripentylsilanol, trihexylsilanol, triheptylsilanol, trioctylsilanol, tri-2-ethylhexylsilanol, trinonylsilanol, tridecylsilanol, triphenylsilanol, (phenyl)(dimethyl)silanol, (phenyl)(diethyl)silanol, (diphenyl)(methyl)silanol, (diphenyl)(ethyl)silanol, diphenylsilanediol, dinaphthylsilanediol, tribenzylsilanol, triphenylethylsilanol, (trimethylsiloxy)(dimethyl)silanol, (triethylsiloxy)(dimethyl)silanol, and the like. Among them, trimethylsilanol and triethylsilanol are particularly preferable.

The metal alkoxide is not particularly limited and, when the metal atom M is Ti, examples thereof include tetramethoxytitanium, tetraethoxytitanium, tetrapropoxytitanium, tetraisopropoxytitanium, tetrabutoxytitanium, tetra-s-butoxytitanium, tetraisobutoxytitanium, tetra-t-butoxytitanium, tetrapentoxytitanium, tetrahexoxytitanium, tetraheptoxytitanium, tetraoctoxytitanium, tetranonanoxytitanium, tetradecanoxytitanium, and the like. When the metal atom M is Zr, examples thereof include tetramethoxyzirconium, tetraethoxyzirconium, tetrapropoxyzirconium, tetraisopropoxyzirconium, tetrabutoxyzirconium, tetra-s-butoxyzirconium, tetraisobutoxyzirconium, tetra-t-butoxyzirconium, tetrapentoxyzirconium, tetrahexoxyzirconium, tetraheptoxyzirconium, tetraoctoxyzirconium, tetranonanoxyzirconium, tetradecanoxyzirconium, and the like. When the metal atom M is Al, examples thereof include trimethoxyaluminum, triethoxyaluminum, tripropoxyaluminum, triisopropoxyaluminum, tributoxyaluminum, tri-s-butoxyaluminum, s-butoxy(diisopropoxy)aluminum, triisobutoxyaluminum, tri t-butoxyaluminum, tripentoxyaluminum, trihexoxyaluminum, triheptoxyaluminum, trioctoxyaluminum, trinonanoxyaluminum, tridecanoxyaluminum, and the like.

When the compound represented by the general formula (2) is a compound represented by the general formula (3), for example, the compound can be obtained by hydrolyzing the metal alkoxide represented by the general formula (2) obtained by the method mentioned above. A general method can be used for hydrolysis. The method includes, for example, a method in which a solvent, water and, if necessary, a catalyst are added to the metal alkoxide represented by the general formula (2), followed by stirring at –20 to 60° C. for about 0.1 to 100 hours. If necessary, hydrolysis by-products (alcohol such as methanol) may be distilled off by distillation under reduced pressure.

The reaction solvent is not particularly limited, but compounds having an alcoholic hydroxyl group, esters, ethers, ketones are suitably used. Specific examples of the alcohol solvent include methanol, ethanol, propanol, isopropanol, butanol, isobutanol, t-butanol, acetol, 3-hydroxy-3-methyl-2-butanone, 5-hydroxy-2-pentanone, 4-hydroxy-4-methyl-2-pentanone (diacetone alcohol), ethyl lactate, butyl lactate, propylene glycol monomethyl ether, propylene glycol monoethyl ether, propylene glycol monopropyl ether, propylene glycol monobutyl ether, propylene glycol mono-t-butyl ether, diethylene glycol monomethyl ether, diethylene glycol monoethyl ether, dipropylene glycol monomethyl ether, 3-methoxy-1-butanol, 3-methyl-3-methoxy-1-butanol, ethylene glycol, propylene glycol, and the like.

Examples of esters include ethyl acetate, propyl acetate, isopropyl acetate, butyl acetate, isobutyl acetate, propylene glycol monomethyl ether acetate, 3-methoxy-1-butyl acetate, 3-methyl-3-methoxy-1-butyl acetate, ethyl acetoacetate, cyclohexanol acetate, and the like.

Examples of ethers include diethyl ether, diisopropyl ether, dibutyl ether, diphenyl ether, diethylene glycol ethyl methyl ether, diethylene glycol dimethyl ether, 1,2-diethoxyethane, dipropylene glycol dimethyl ether, and the like.

Specific examples of the ketone solvent include methyl isobutyl ketone, diisopropyl ketone, diisobutyl ketone, acetylacetone, cyclopentanone, cyclohexanone, cycloheptanone, and the like.

Examples of other solvents that can be preferably used include propylene carbonate, N-methylpyrrolidone, and the like.

By adjusting the amount of water to be used in the hydrolysis reaction, the amount of the hydroxy group of the metal compound represented by the general formula (3) can be adjusted. For example, in the case of a metal compound in which y=1, that is, a metal compound having one hydroxy group, it is possible to obtain by adding 1 mol of water to 1 mol of the metal alkoxide. By adding 1 mol of water to 1 mol of alkoxy group which is a hydrolyzable group, it is possible to obtain a metal compound in which all alkoxy groups are hydrolyzed. The amount of water added is preferably 0.1 to 2 mols based on the alkoxy group.

There is no particular limitation on the catalyst to be optionally added, and an acidic catalyst or a basic catalyst is preferably used. Specific examples of the acidic catalyst include hydrochloric acid, nitric acid, sulfuric acid, hydrofluoric acid, phosphoric acid, acetic acid, trifluoroacetic acid, formic acid, polyvalent carboxylic acid or an anhydride thereof, and an ion exchange resin. Specific examples of the basic catalyst include, triethylamine, tripropylamine, tributylamine, tripentylamine, trihexylamine, triheptylamine, trioctylamine, diethylamine, dipropylamine, dibutylamine, diisobutylamine, dipentylamine, dihexylamine, diheptylamine, dioctylamine, triethanolamine, diethanolamine, dicyclohexylamine, dicyclohexylmethylamine, sodium hydroxide, potassium hydroxide, alkoxysilane having an amino group, and ion exchange resin. The amount of the catalyst added is preferably 0.01 to 30 parts by weight based on 100 parts by weight of the siloxy group-containing compound represented by the general formula (2).

(Method for Producing Polymetalloxane)

A general method can be used for hydrolysis, partial condensation, and polymerization of the compound represented by the general formula (2). For example, the reaction conditions for the hydrolysis are preferably such that water is added to the compound represented by the general formula (2) over 1 to 180 minutes in a solvent, and then a reaction is performed at room temperature to 110° C. for 1 to 180 minutes. By performing the hydrolysis reaction under such conditions, rapid reaction can be suppressed. The reaction temperature is preferably 30 to 150° C. A catalyst may be optionally added.

As the reaction condition for partial condensation and polymerization, a hydrolyzate is obtained by a hydrolysis reaction of the compound represented by the general formula (2), and then the reaction solution is directly heated at 50° C. to 180° C. for 1 to 100 hours. To increase the degree of polymerization of the polymetalloxane, reheating or the addition of a catalyst may be performed. After the hydrolysis reaction, an appropriate amount of the thus produced alcohol may be distilled off and removed by heating and/or evacuation, followed by addition of an optional solvent.

The solvent is not particularly limited, but compounds having an alcoholic hydroxyl group, esters, ethers, and ketones are preferably used. When these solvents are used, the stability of the polymetalloxane can be improved, thus making it possible to improve the transparency of the resulting coating film.

Specific examples of the alcohol-based solvent include methanol, ethanol, n-propanol, isopropanol, n-butanol, isobutanol, t-butanol, acetol, 3-hydroxy-3-methyl-2-butanone, 5-hydroxy-2-pentanone, 4-hydroxy-4-methyl-2-pentanone (diacetone alcohol), ethyl lactate, butyl lactate, propylene glycol monomethyl ether, propylene glycol monoethyl ether, propylene glycol mono-n-propyl ether, propylene glycol mono-n-butyl ether, propylene glycol mono-t-butyl ether, diethylene glycol monomethyl ether, diethylene glycol monoethyl ether, dipropylene glycol monomethyl ether, 3-methoxy-1-butanol, 3-methyl-3-methoxy-1-butanol, ethylene glycol, propylene glycol, and the like.

Examples of esters include ethyl acetate, n-propyl acetate, isopropyl acetate, n-butyl acetate, isobutyl acetate, propylene glycol monomethyl ether acetate, 3-methoxy-1-butyl acetate, 3-methyl-3-methoxy-1-butyl acetate, ethyl acetoacetate, cyclohexanol acetate, and the like.

Examples of ethers include diethyl ether, diisopropyl ether, di-n-butyl ether, diphenyl ether, diethylene glycol ethyl methyl ether, diethylene glycol dimethyl ether, 1,2-dimethoxyethane, 1,2-diethoxyethane, dipropylene glycol dimethyl ether, and the like.

Specific examples of the ketone solvent include methyl isobutyl ketone, diisopropyl ketone, diisobutyl ketone, acetylacetone, cyclopentanone, cyclohexanone, cycloheptanone, and the like.

Examples of other solvents, which can be preferably used, include propylene carbonate, N-methylpyrrolidone, and the like.

By adjusting the amount of water added in the hydrolysis reaction, it is possible to adjust the degree of hydrolysis of the compound represented by the general formula (2). The amount of water is preferably 0.1 to 2 mols based on 1 mol of the alkoxy group.

There is no particular limitation on the catalyst to be optionally added, and an acidic catalyst or a basic catalyst is preferably used. Specific examples of the acidic catalyst include hydrochloric acid, nitric acid, sulfuric acid, hydrofluoric acid, phosphoric acid, acetic acid, trifluoroacetic acid, formic acid, polyvalent carboxylic acid or an anhydride thereof, and an ion exchange resin. Specific examples of basic catalysts include triethylamine, tripropylamine, tributylamine, tripentylamine, trihexylamine, triheptylamine, trioctylamine, diethylamine, dipropylamine, dibutylamine, diisobutylamine, dipentylamine, dihexylamine, diheptylamine, dioctylamine, triethanolamine, diethanolamine, dicyclohexylamine, dicyclohexylmethylamine, sodium hydroxide, potassium hydroxide, alkoxysilane having an amino group, and ion exchange resin.

More preferred catalyst is a basic catalyst. By using a basic catalyst, particularly a high molecular weight polymetalloxane can be obtained. Among basic catalysts, tripropylamine, triisobutylamine, tripentylamine, triisopentylamine, trihexylamine, triheptylamine, trioctylamine, dibutylamine, diisobutylamine, dipentylamine, dihexylamine, diheptylamine, and dioctylamine are particularly preferred.

From the viewpoint of the storage stability of the composition, it is preferable that the above-mentioned catalyst is not contained in the polymetalloxane solution after hydrolysis, partial condensation, and polymerization, and the catalyst can be optionally removed. There is no particular limitation on the removal method and washing with water and/or a treatment with an ion exchange resin is/are preferred from the viewpoint of easy operation and removability. Washing with water is a method in which a polymetalloxane solution is diluted with an appropriate hydrophobic solvent and washed several times with water, and then the obtained organic layer is concentrated by an evaporator. The treatment with an ion exchange resin is a method in which a polysiloxane solution is brought into contact with an appropriate ion exchange resin.

(Composition of Polymetalloxane)

The polymetalloxane of the present invention can be mixed with a solvent and other necessary components to form a composition.

The polymetalloxane of the present invention is preferably diluted with a solvent to adjust the solid component concentration. The solvent is not particularly limited and is preferably the same solvent as that used in the synthesis of the polymetalloxane. The solid component concentration of the solution containing the polymetalloxane is preferably set at 0.1 to 50% by weight. When the solid component concentration is set in the above range, the film thickness of the coating film is satisfactorily controlled.

During the adjustment of the solid content of the polymetalloxane solution, other components may be added. Examples of other components include inorganic particles, a surfactant, a silane coupling agent, a crosslinking agent, a crosslinking accelerator, and the like.

The inorganic particles are preferably used for improving a refractive index of the cured film. The inorganic particles are preferably (b1) one or more particles selected from aluminum compound particles, tin compound particles, titanium compound particles, and zirconium compound particles, or (b2) composite particles of one or more metal compounds selected from an aluminum compound, a tin compound, a titanium compound, and a zirconium compound, and a silicon compound. Hereinafter, these particles are collectively referred to as "metal compound particles". The refractive index can be further improved by adding these particles.

The average particle size of the metal compound particles is preferably 1 nm to 400 nm. When the average particle size is 1 nm or more, it is possible to further suppress the occurrence of cracks during formation of a thick film, and the average particle size is more preferably 5 nm or more. When the average particle size is 400 nm or less, the refractive index can be improved without causing deterioration of the transparency of the cured film to visible light, and the average particle size is more preferably 70 nm or less.

Examples of the metal compound particles include "Optolake TR-502" and "Optolake TR-504" of tin oxide-titanium oxide composite particles, "Optolake TR-503", "Optolake TR-513", "Optolake TR-520", "Optolake TR-527", "Optolake TR-528", "Optolake TR-529", "Optolake TR-543", "Optolake TR-544", and "Optolake TR-550" of silicon oxide-titanium oxide composite particles, and "Optolake TR-505" of titanium oxide particles (trade names, all of which are manufactured by Catalysts & Chemicals Ind. Co., Ltd.); NOD-7771GTB (trade name, manufactured by Nagase ChemteX Corporation); zirconium oxide particles (manufactured by Kojundo Chemical Laboratory Co., Ltd.); tin oxide-zirconium oxide composite particles (manufactured by Catalysts & Chemicals Ind. Co., Ltd.); tin oxide particles (manufactured by Kojundo Chemical Laboratory Co., Ltd.); "BIRAL" Zr-C20 (titanium oxide particles; average particle diameter of 20 nm, manufactured by Taki Chemical Co., Ltd.); ZSL-10A (titanium oxide particles, average particle diameter of 60 to 100 nm, manufactured by DAIICHI KIGENSO KAGAKU KOGYO CO., LTD.); NanoUse OZ-30M (titanium oxide particles, average particle diameter of 7 nm, manufactured by Nissan chemical industries, Ltd.), SZR-M or SZR-K (zirconium oxide particles, both of which are manufactured by SAKAI CHEMICAL INDUSTRY CO., LTD.); HXU-120JC (zirconia oxide particles, manufactured by SUMITOMO OSAKA CEMENT Co., Ltd.), ZR-010 (zirconia oxide particles, manufactured by SOLAR CO., LTD.), or ZRPMA (zirconia particles, manufactured by C.I. Kasei CO., LTD.).

The surfactant is preferably used for improving the flow property during coating. The surfactant may remain on the cured film.

There is no particular limitation on the type of the surfactant, and it is possible to use, for example, fluorine-based surfactants such as "MEGAFAC (registered trademark)" F142D, MEGAFAC F172, MEGAFAC F173, MEGAFAC F183, MEGAFAC F444, MEGAFAC F445, MEGAFAC F470, MEGAFAC F475, and MEGAFAC F477 (all of which are manufactured by DIC Corporation) and NBX-15, FTX-218, and DFX-18 (manufactured by Neos Corporation); silicone-based surfactants such as BYK-333, BYK-301, BYK-331, BYK-345, and BYK-307 (manufactured by BYK-Chemie Japan); polyalkylene oxide-based surfactants; and poly(meth)acrylate-based surfactants. Two or more types of these surfactants may be used.

The amount of the surfactant added is preferably 0.001 to 10 parts by weight, and more preferably 0.01 to 1 parts by weight, based on 100 parts by weight of the polymetalloxane.

The silane coupling agent is preferably used for improving the adhesion to the substrate. The silane coupling agent is not particularly limited, and it is possible to use, for example, vinyltrimethoxysilane, vinyltriethoxysilane, 2-(3,4 epoxycyclohexyl)ethyltrimethoxysilane, 3-glycidoxypropyltrimethoxysilane, 3-methacryloxypropylmethyldimethoxysilane, 3-methacryloxypropyltrimethoxysilane, 3-acryloxypropyltrimethoxysilane, 3-aminopropyltrimethoxysilane, 3-aminopropyltriethoxysilane, 3-triethoxysilyl-N-(1,3-dimethyl-butylidene) propylamine, 3-mercaptopropylmethyldimethoxysilane, 3-mercaptopropyltrimethoxysilane, 3-isocyanatopropyltriethoxysilane, diphenyldimethoxysilane, trimethylsilanol, diphenylsilanediol, and the like.

The amount of the silane coupling agent added is preferably from 0.1 to 50 parts by weight, more preferably from 1 to 20 parts by weight, based on 100 parts by weight of the polymetalloxane.

The crosslinking agent and the crosslinking accelerator are preferably used for improving the chemical resistance of the cured film. The type of the crosslinking agent and the crosslinking accelerator is not particularly limited, and it is possible to use, for example, mono-s-butoxyaluminum diisopropylate, aluminum-s-butyrate, ethylacetoacetate aluminum diisopropylate, aluminum tris(ethyl acetate), alkylacetoaluminum diisopropylate, aluminum monoacetylacetonatebis(ethylacetoacetate), aluminum tris(acetylacetonate), zirconium tris(acetylacetate), zirconium tris(ethylacetoacetate), titanium tris(acetylacetate), titanium tris (ethylacetoacetate), and the like.

The total content of the crosslinking agent and the crosslinking accelerator is preferably 0.1 to 50 parts by weight, and more preferably 1 to 20 parts by weight, based on 100 parts by weight of the polymetalloxane. The crosslinking agent and the crosslinking accelerator may be used alone or used in combination.

Examples of the substrate include, but are not particularly limited to, silicon wafer, sapphire wafer, glass, and optical film. Examples of the glass include alkali glass, alkali-free glass, thermally tempered glass, or chemically tempered glass. Examples of the optical film include a film made of acrylic resin, polyester resin, polycarbonate, polyarylate, polyether sulfone, polypropylene, polyethylene, polyimide, or cycloolefin polymer.

(Step of Forming Cured Film)

The polymetalloxane or the composition containing the same of the present invention can be heated to form a cured film. The thus obtained cured film is a cured film mainly composed of a resin having a metal atom having a high electron density in the main chain, so that the density of metal atoms in the cured film can be increased, thus easily obtaining a high refractive index. Since it becomes a dielectric containing no free electrons, high transparency and heat resistance can be obtained.

Known methods can be used for coating the solution containing the polymetalloxane. Examples of the apparatus used for coating include full-surface coating apparatuses such as spin coating, dip coating, curtain flow coating, spray coating, or slit coating, or printing apparatus such as screen printing, roll coating, micro gravure coating, or ink jet.

After coating, heating (pre-baking) may be optionally performed using a heating device such as a hot plate or an oven. Pre-baking is preferably performed at a temperature in a range of 50 to 150° C. for 30 seconds to 30 minutes to form a pre-bake film. By performing pre-baking, the film thickness uniformity can be improved. The film thickness after pre-baking is preferably 0.1 to 15 μm.

The coating film or the prebake film is heated (cured) at a temperature in a range of 150° C. to 450° C. for 30 seconds to 2 hours using a heating device such as a hot plate or an oven, thus making it possible to obtain a cured film containing a polymetalloxane. The thickness of the cured film is preferably 0.1 to 15 μm.

The resulting cured film preferably has a refractive index of 1.58 or more and 2.20 or less at a wavelength of 550 nm, and more preferably 1.65 or more and 2.10 or less.

The refractive index of the cured film can be measured by the following method. Using a spectroscopic ellipsometer, change in the polarization state of reflected light from the cured film and the substrate is measured to obtain a phase difference with incident light and a spectrum of an amplitude reflectance. By fitting the dielectric function of the calculation model so that it approaches the obtained spectrum, a refractive index spectrum is obtained. By reading the refractive index value at a wavelength of 550 nm from the obtained refractive index spectrum, the refractive index of the cured film can be obtained.

The cured film thus obtained preferably has a light transmittance of 90% or more per 1 μm of a film thickness at a wavelength of 400 nm. The light transmittance can be measured by the following method as long as it is formed on a transparent substrate. First, ultraviolet-visible absorption spectrum of the substrate is measured using a spectrophotometer, and the spectrum is used as a reference. Next, the ultraviolet-visible absorption spectrum of the cured film formed on the transparent substrate is measured, and the ultraviolet-visible absorption spectrum of the cured film is calculated from the difference from the reference. Using the thus obtained ultraviolet-visible absorption spectrum and the film thickness of the cured film, the light transmittance per 1 μm of the film thickness at a wavelength of 400 nm of the micro lens is calculated.

The light transmittance of the cured film formed on an opaque substrate such as a silicon wafer can be measured by the following method. Using a spectroscopic ellipsometer, change in the polarization state of reflected light from the cured film and the substrate is measured to obtain a phase difference with incident light and a spectrum of the amplitude reflectance. By fitting the dielectric function of the calculation model so that it approaches the obtained spectrum, an extinction coefficient spectrum is obtained. The extinction coefficient at a wavelength of 400 nm is read from the obtained extinction coefficient spectrum, and light transmittance for obtaining the light transmittance (%) in terms of a film thickness of 1 μm at a wavelength of 400 nm by using the following equation:

Light transmittance=exp($-4\pi kt/\lambda$)

where k is an extinction coefficient, t is a converted film thickness (μm), and λ is a measurement wavelength (nm). In this measurement, to obtain the light transmittance in terms of 1 μm, t is 1 (μm).

(Applications)

Since the above-mentioned cured film is excellent in refractive index and transparency, it is suitably used for electronic components such as a solid state image sensor, an optical filter, a display, and the like. More specifically, examples thereof include a microlens for condensing light and an optical waveguide formed in a solid state image sensor such as a back-illuminated CMOS image sensor, an antireflection film provided as an optical filter, a flattening material of a display TFT substrate, a color filter such as a liquid crystal display and a protective film thereof, a phase shifter, and the like.

Among them, since it is possible to achieve both high transparency and high refractive index at the same time, it is particularly suitably used as a microlens for condensing light formed on a solid-state image pickup element or an optical waveguide connecting a light collecting microlens and a photosensor section. It is also possible to use as a buffer coat, an interlayer insulating film, and various protective films for semiconductor devices.

(Application for Touch Sensor)

The cured film obtained from the polymetalloxane of the present invention or the composition thereof is suitable for use as a touch sensor member used in a smartphone or a tablet terminal, since it is possible to achieve both high transparency and high refractive index at the same time. More specifically, examples thereof include an insulating layer thin film formed on the upper or lower portion of the transparent conductive film used for forming a sensor.

One of the problems of the touch sensor and the display using it is deterioration of appearance of the terminal due to visual recognition of a transparent conductive film pattern such as indium tin oxide (hereinafter abbreviated to "ITO"). There has been developed, as typical technology for suppressing the visibility of the transparent electrode pattern, technology in which an insulating layer thin film is formed on the upper or lower portion of a transparent electrode thereby reducing interface reflection, leading to suppression of visibility of a transparent electrode pattern (e.g., JP 1-205122 A, JP 6-033000 A, and JP 8-240800 A). In this insulating layer thin film, because of high refractive index of the transparent electrode pattern, high refractive index and transparency are required.

There has been developed, as technology for reducing the visibility of the transparent electrode pattern, technology in which thin films of $Nb_2O_3$ and $SiO_2$ are formed as an undercoat layer or a topcoat layer (for example, JP 2010-152809 A and JP 2010-086684 A). There has also been developed technology in which an organic thin film and a silicon oxide thin film each having a refractive index of 1.58 to 1.85 are formed (e.g., WO 2014/119372) for the purpose of cost reduction and saving process. According to this technology, using an organic composition containing titanium oxide particles having high refractive index alone as a single substance, titanium oxide fine particles such as barium titanate particles, or zirconium oxide particles such as zirconium oxide particles, the refractive index is controlled in a desired value range. Alternatively, a substituent having a high refractive index is introduced into the organic component to control the refractive index in a desired range.

However, in the case of controlling the refractive index using conventional metal oxide particles, in addition to a problem such as expensive metal oxide particles, increasing the content ratio of the metal oxide particles causes poor dispersion, leading to a problem such as precipitation of particles. When the refractive index is controlled by a substituent having a high refractive index, there is a limitation on a changeable range of the refractive index, and thus it is difficult to achieve a high refractive index exceeding 1.8.

Therefore, it is possible to easily control the refractive index by using the cured film obtained from the polymetalloxane of the present invention or the composition thereof, thus making it possible to provide a substrate in which the visibility of the transparent conductive film pattern is significantly reduced, easily at low cost.

Specifically, when a touch sensor has a member having a portion in which a transparent conductive thin film (I) and a cured film (II) obtained from the polymetalloxane of the present invention or the composition thereof are laminated in this order from the upper surface of a transparent underlying base material, it is possible to weaken the reflected light at the upper interface and the lower interface of the transparent conductive thin film (I) formed on the lower layer, thus reducing the pattern visibility of the transparent conductive thin film. It is also possible to improve the durability of the touch sensor since the transparent conductive film is protected with a thin film.

Detailed description will be made of the member having a portion in which a transparent conductive thin film (I) and a cured film (II) obtained from the polymetalloxane of the present invention or the composition thereof are laminated in the order.

There is no particular limitation on the material of the transparent underlying base material as long as it has a function of transmitting light, and preferred is a material in which a total line transmittance per 0.1 mm of a thickness (in accordance with JIS K 7361-1: 1997) is 80%, and examples thereof include glass and an optical film. From the viewpoint of the heat resistance and chemical resistance, the material is more preferably glass. Examples of the glass include alkali glass, alkali-free glass, thermally tempered glass, or chemically tempered glass, and the glass is preferably thermally tempered glass or chemically tempered glass which is widely used as a cover glass of a touch panel. Examples of the optical film include a film made of an acrylic resin, a polyester resin, a polycarbonate, a polyarylate, a polyether sulfone, a polypropylene, a polyethylene, a polyimide, or a cycloolefin polymer. Among them, an acrylic resin, a polyester resin, a polycarbonate, or a cycloolefin polymer is preferable, from the viewpoint of the transparency. The acrylic resin is preferably polymethyl methacrylate. The polyester resin is preferably polyethylene terephthalate, polyethylene naphthalate, or polybutylene terephthalate. The polycarbonate is preferably a resin obtained by polycondensation of bisphenol A and phosgene. The polyimide is preferably a resin containing an aliphatic carboxylic acid dianhydride and/or an aliphatic diamine as a monomer, from the viewpoint of the transparency. The cycloolefin polymer is preferably, for example, a polymer obtained by addition polymerization or ring-opening metathesis polymerization of cyclohexene or norbornene or derivatives thereof.

As the transparent conductive thin film (I), an ITO thin film is most common. In the present application, description will be made by way of an ITO thin film as an example, but the present invention is not limited thereto. A method of forming a transparent conductive thin film is preferably a sputtering method since it is easy to obtain a thin film having low resistance and precise film thickness control is possible. The film thickness of the transparent conductive thin film (I) is preferably 1 to 200 nm.

The film thickness and the refractive index of the cured film (II) obtained from the polymetalloxane of the present invention or the composition thereof laminated on the top surface of the transparent conductive thin film (I) are preferably 0.01 to 3 μm and 1.58 to 1.95, respectively. Within the above range, it is possible to control the phase and intensity of the reflected light at the upper interface and the lower interface of the thin film (II) containing the composition. As mentioned above, the reflected light at the upper interface and the lower interface of the transparent conductive thin film (I) is weakened, thus making it possible to reduce the pattern visibility of the transparent conductive thin film. When the film thickness of the thin film (II) containing the composition is set in the above range, it is possible to control the phase, thus exerting sufficient effect of reducing the pattern visibility. When the refractive index of the thin film (II) containing the composition is set in the above range, it is possible to control the intensity of the reflected light, thus exerting sufficient effect of reducing the pattern visibility. The film thickness and the refractive index are more preferably 0.1 to 2.5 μm and 1.65 to 1.95, and particularly preferably 0.15 to 2 μm and 1.80 to 1.95, respectively.

It is preferred to have a portion in which a silicon oxide thin film (III) and/or a transparent pressure-sensitive adhesive thin film (IV) having a refractive index of 1.46 to 1.53 is/are laminated on the upper surface of the cured film (II) obtained from the polymetalloxane of the present invention or the composition thereof.

By having the silicon oxide thin film (III), it is possible to control the intensity of the reflected light of the lower interface (i.e., reflected light of the upper interface of the cured film (II) obtained from the polymetalloxane or the composition thereof). At the same time, the underlying metal including the transparent conductive thin film (I) can be protected, thus enabling an improvement in reliability of the touch sensor in the touch sensor application.

The film thickness of the silicon oxide thin film (III) is preferably 0.01 to 10 μm. If the film thickness is less than 0.01 μm, because of an influence of reflected light on the upper interface, it is difficult to obtain the effect of reducing the pattern visibility, thus failing to obtain a function of protecting the underlying metal. If the thickness exceeds 10 μm, cracks easily occur due to slight distortion, leading to deterioration of the reliability and appearance of the touch panel.

Examples of the method of forming a silicon oxide thin film (III) include a dry process method such as a sputtering method, a vacuum deposition method (electron beam method), an ion plating method (IP method), or a chemical vapor deposition (CVD) method, or a wet process method such as spin on glass (SOG). Among them, the CVD method is preferable since it can form a thin film with relatively few defects at a relatively low temperature.

The transparent pressure-sensitive adhesive thin film (IV) refers to a thin film formed with a transparent pressure-sensitive adhesive. Here, the transparent pressure-sensitive adhesive means a material that transmits light and has pressure-sensitive adhesion.

The film thickness of the transparent pressure-sensitive adhesive thin film (IV) is preferably 1 to 200 μm from the viewpoint of the pressure-sensitive adhesion and transparency.

The pressure-sensitive adhesive force of the transparent pressure-sensitive adhesive is preferably 3 to 100 N/20 mm. The transmittance of the transparent pressure-sensitive adhesive is preferably 90% or more in view of the total line transmittance (JIS K 7361-1: 1997) from the viewpoint of the appearance of the touch sensor.

Examples of the transparent pressure-sensitive adhesive include a thermosetting pressure-sensitive adhesive or a UV-curable pressure-sensitive adhesive. Examples of the thermosetting transparent pressure-sensitive adhesive having a refractive index of 1.46 to 1.52 include a thermosetting transparent pressure-sensitive adhesive containing an alkyl (meth) acrylate having 1 to 20 carbon atoms, a (meth) acrylate having a hydroxyl group and/or a copolymer having a (meth) acrylic acid derivative having a carboxyl group as a constituent monomer, or a polyfunctional isocyanate compound and/or a polyfunctional epoxy compound. Examples of the UV-curable transparent pressure-sensitive adhesive having a refractive index of 1.46 to 1.52 include a UV-curable transparent pressure-sensitive adhesive containing a monofunctional or polyfunctional (meth) acrylate monomer and/or an oligomer and a photopolymerization initiator as a main component.

It is possible to use, as such transparent pressure-sensitive adhesives, an optical clear adhesive (OCA) material (common name of thermosetting adhesive) or an optical clear adhesive resin (OCR) material (common name of UV curing type pressure-sensitive adhesive) which is used to superpose various substrates one upon another. It is possible to use, as the transparent pressure-sensitive adhesive film (IV) formed from the transparent pressure-sensitive adhesive as mentioned above, a pressure-sensitive adhesive provided with a commercially available multifunctional film such as an antiscattering film.

Examples of commercially available OCA materials capable of forming a transparent pressure-sensitive adhesive film (IV) include 8171CL, 8172CL, 8146-1, or 8146-2 (all of which are manufactured by Sumitomo 3M Limited); CS9622T, CS9621T, or CS9070 (all of which are manufactured by Nitto Denko Corporation); TE-9000, TE-7000, TE-8500, or DA-5000H (all of which are manufactured by Hitachi Chemical Co., Ltd.), or MO-3010 or MO-T010 (all of which are manufactured by LINTEC Corporation). Examples of commercially available OCR materials capable of forming the transparent pressure-sensitive adhesive film (IV) include XV-SV-B1 or XV-7811 (all of which are manufactured by Panasonic Corporation) or UVP-1003, UVP-1100, UVP-7100, or UVP-7000 (all of which are manufactured by Toagosei Chemical Industry Co., Ltd.). Examples of commercially available multifunctional films with a transparent pressure-sensitive adhesive capable of forming a transparent pressure-sensitive adhesive film (IV) include HA-110, HA-115, HA-116, HA-116, or HA-203 used widely as an antiscattering film (all of which are manufactured by LINTEC Corporation), or HC1100F-BP or HC2120F-BP (all of which are manufactured by DIC Corporation).

A member having a portion in which a thin film is laminated in the order of the transparent conductive thin film (I) and the cured film (II) obtained from the polymetalloxane of the present invention or the composition thereof is suitably used for display applications. Examples thereof include a resistive touch panel, a capacitive touch panel, and a TFT substrate, and the member is preferably used for a capacitive touch panel, and more preferably a cover glass integrated electrostatic capacitive touch panel.

(Lens Application)

Since the cured film obtained from the polymetalloxane of the present invention is excellent in refractive index and transparency and is suitably used for lenses. More specifically, it can be suitably used for light collecting microlens formed in a solid state image sensor such as back-illuminated CMOS image sensors.

The solid state image sensor includes a large number of photoelectric conversion elements arranged in a matrix on a semiconductor substrate. In front of each photoelectric conversion element, microlenses for focusing incident light on a photoelectric conversion element are arranged for each photoelectric conversion element. Microlenses are required to have high refractive index and transparency from the viewpoint of the light collection efficiency.

Examples of a manufacturing method of such a microlens include a method using dry etching. This method is as follows. A cured film of the lens material is formed on the substrate. Next, a photoresist pattern is formed on the cured film in the same shape as that of the microlens. Then, both the photoresist and the cured film are dry-etched, and the pattern of the photoresist is transferred to the cured film to obtain a microlens.

Since the cured film obtained from the polymetalloxane of the present invention becomes a dielectric containing no free electrons, high transparency and heat resistance can be obtained. It is possible to form a cured film mainly composed of a resin component, and the reactivity between the cured film an etching gas during dry etching can be made substantially uniform throughout the film. Therefore, a difference in dry etching rate does not occur locally, and a smooth microlens having no surface roughness can be obtained.

There is no particular limitation on the method of manufacturing a lens made of a cured film of polymetalloxane, and it is preferred to include the steps of forming a cured film containing the polymetalloxane of the present invention on a substrate, forming a photoresist pattern on the cured film, and dry-etching the photoresist pattern and the cured film. Details will be described in each step.

Examples of the above-mentioned substrate include, but are not particularly limited to, a silicon wafer, a sapphire wafer, glass, and an optical film. Example of the glass include alkali glass, alkali-free glass, thermally tempered glass, or chemically tempered glass. Examples of the optical film include a film made of an acrylic resin, a polyester resin, a polycarbonate, a polyarylate, a polyether sulfone, a polypropylene, a polyethylene, a polyimide, or a cycloolefin polymer.

The method for forming a cured film containing a polymetalloxane on a substrate is preferably a method in which a solution containing a polymetalloxane is coated and heated to form a cured film.

The photoresist pattern is obtained by forming a photoresist layer on the cured film containing the polymetalloxane and patterning the photoresist layer by photolithography.

The photoresist layer can be obtained by coating a commercially available photoresist. As a coating method, a known method can be used. Examples of the apparatus used for coating include full-surface coating apparatuses such as spin coating, dip coating, curtain flow coating, spray coating, or slit coating, or printing apparatus such as screen printing, roll coating, micro gravure coating or ink jet.

After coating, heating (pre-baking) may be optionally performed using a heating device such as a hot plate or an oven. Pre-baking is preferably performed at a temperature in a range of 50 to 150° C. for 30 seconds to 30 minutes to form a pre-bake film. By performing pre-baking, film thickness uniformity can be improved. The film thickness after pre-baking is preferably 0.1 to 15 µm.

The patterning method of the photoresist layer by photolithography is not particularly limited, and it is preferred that pattern exposure is performed via a desired mask using an ultraviolet visible exposure machine such as a stepper, a mirror projection mask aligner (MPA), a parallel light mask aligner (PLA), followed by development with a known developer for photoresist to obtain a pattern.

As a mask used for pattern exposure, a mask designed to obtain a dot-shaped or square-shaped photoresist pattern of 0.1 µm to 10 µm is preferably used. The photoresist pattern can be thermally melted, if necessary. By performing thermal melting, the photoresist pattern can be made convex. The conditions for thermal melting are not particularly limited, and it is preferred to heat at a temperature in a range of 50° C. to 300° C. for about 30 seconds to 2 hours using a heating device such as a hot plate or an oven.

A microlens can be obtained by dry-etching a photoresist pattern and a cured film containing polymetalloxane on the whole surface. The dry etching is preferably performed using a reactive ion etching apparatus (RiE apparatus), and using as a process gas $CHF_3$ (methane trifluoride), $CF_4$ (methane tetrafluoride), oxygen, or a mixed gas thereof. By performing such dry etching, the photoresist pattern and the cured film containing the polymetalloxane can be simultaneously etched, thus making it possible to form the cured film containing the polymetalloxane into a microlens shape.

When dry etching residues of the photoresist pattern are generated after dry etching, the photoresist may be optionally removed if necessary. Examples of the removal method include, but are not limited to, asking using oxygen as a process gas, or immersion in a commercially available resist stripping solution.

(Organic EL Application)

The cured film obtained from the polymetalloxane of the present invention is suitably used for organic EL elements and organic EL lighting applications. More specifically, examples thereof include an insulating layer thin film formed on the upper portion or the lower portion of the transparent conductive film used for the organic EL element or the organic EL lighting.

Currently, the organic EL is a new light source that performs surface light emission and is expected to be applied to next-generation displays and lighting. The organic EL has a structure including an organic layer such as a light emitting layer, a layer for controlling carrier injecting properties and transporting properties between electrodes. The organic EL has a problem such as low light extraction efficiency, i.e., low efficiency with which the generated light comes out of the device. Because of large refractive index of the organic layer and the refractive index of the transparent electrode, in the case of propagating to the substrate (n is about 1.5) having a low refractive index or the air (n is about 1.0), most of the light is totally reflected at the interface, leading to decrease in extraction efficiency.

Therefore, by setting the cured film obtained from the polymetalloxane of the present invention on the upper part or the lower part of the transparent electrode, it is possible to control the phase and intensity of the reflected light at the upper interface and the lower interface of the cured film, thus suppressing reflection at the upper interface or the lower interface, leading to significant improvement in light extraction efficiency.

(Building Material Use)

The metalloxane of the present invention can be formed into a metal oxide film by coating and curing, so that the metalloxane can be used as a building material. More specifically, examples thereof include a flame retardant material and a hydrophilicity imparting material. Since the polymetalloxane of the present invention serves as a non-flammable layer, a flame retardant can impart flame retardancy by the effect of blocking combustion. Since a film having high hydrophilicity can be formed by coating the surface of the building material with the polymetalloxane of the present invention, so that an antifouling effect can be expected.

(Radionuclide Generator Application)

The polymetalloxane of the present invention can be used for radionuclide generator applications. Specifically, it is a radionuclide generator having a column packed with the polymetalloxane of the present invention.

Currently, in the medical field, radionuclides are used as a radioactive diagnostic agent and a radiotherapeutic agent. $^{99m}$Tc (technetium-99m, half-life of 6.01 hours), which is a radionuclide, is most frequently used as a radioactive diagnostic agent.

$^{99m}$Tc is produced by β decay of the parent nuclide $^{99}$Mo (molybdenum-99, half-life of 65.9 hours). That is, $MoO_3$ pellet containing $^{99}$Mo produced by nuclear fission method or activation method is converted into an aqueous sodium molybdate solution and the aqueous solution is passed through a column packed with an adsorbent to trap Mo in the adsorbent. Among trapped Mo, only $^{98}$Mo causes β decay to produce $^{98m}$Tc. By passing water through the column in this state, $^{98m}$Tc can be selectively taken out.

The nuclear fission method in the method of producing $^{99}$Mo is a method in which $^{235}$U (uranium-235) in enriched uranium is irradiated with neutrons to cause a fission reaction and $^{99}$Mo is taken out through a complicated process. However, this method has a disadvantage that a large amount of radioactive waste is produced. Meanwhile, in the activation method, naturally occurring $^{98}$Mo (molybdenum-98) is irradiated with neutrons to produce $^{99}$Mo. This activation method has an advantage that no radioactive waste is generated but has a problem that $^{99}$Mo thus generated has low specific radioactivity. Therefore, there is a demand for an adsorbent having high adsorption ability and a column.

An inorganic polymer zirconium chloride compound has been developed as an adsorbent having high adsorption performance. However, in this compound, when an aqueous sodium molybdate solution is passed through a column, a chloro group at the end of the compound is hydrolyzed to produce hydrogen chloride. This hydrogen chloride is a corrosive gas and has a problem in safety. Therefore, there has been required an adsorbent which does not generate hydrogen chloride and has high adsorption performance.

The polymetalloxane of the present invention has a ($R^3_3SiO$—) group and/or a hydroxyl group at the end and therefore serves as a Mo adsorption site. Therefore, like the inorganic polymer zirconium chloride, the polymetalloxane has high adsorption performance. However, the polymetalloxane does not produce corrosive gas such as hydrogen chloride, so that the polymetalloxane can be suitably used as an adsorbent having high adsorption performance and high safety.

By using a column packed with polymetalloxane of the present invention as a radionuclide generator, $^{98m}$Tc can be efficiently produced because of its high adsorption capability, so that the apparatus can be reduced in size and weight.

EXAMPLES

The present invention will be described more specifically by way of Synthesis Examples and Examples, but the present invention is not limited to these Examples.

In each Synthesis Example, analysis by Fourier transform infrared spectroscopy (hereinafter abbreviated to FT-IR) was performed by the following method. First, using a Fourier transform infrared spectrometer (FT 720, manufactured by Shimadzu Corporation), two silicon wafers superposed one upon another were measured and used as a baseline. Next, one drop of a metal compound or a solution thereof was dropped on a silicon wafer and the silicon wafer was sandwiched by another silicon wafer, and the thus obtained sample was used as a measurement sample. An absorbance of the compound or a solution thereof was calculated from the difference between the absorbance of the measurement sample and the absorbance of the baseline and the absorption peak was read.

(Synthesis Example 1) Synthesis of Titanium Compound (T1)

In a three-necked flask having a capacity of 500 ml, 34.0 g (0.1 mol) of tetrabutoxytitanium was charged and the flask was immersed in an oil bath at 40° C., followed by stirring for 30 minutes. Thereafter, using a dropping funnel, 9.0 g (0.1 mol) of trimethylsilanol was added over 1 hour and, after the addition, the mixture was stirred for additional 1 hour. The content of the flask was transferred to a 200 ml recovery flask, and butanol thus formed was distilled off under reduced pressure to obtain a colorless liquid titanium compound (T1).

Analysis of the titanium compound (T1) by FT-IR revealed that an absorption peak of Ti—O—Si (958 cm$^{-1}$) was formed and there was no absorption of silanol (883 cm$^{-1}$), and thus the obtained titanium compound (T1) is tributoxy(trimethylsiloxy)titanium.

(Synthesis Example 2) Synthesis of Titanium Compound (T2)

In a three-necked flask having a capacity of 500 ml, 28.4 g (0.1 mol) of tetraisopropoxytitanium was charged and the flask was immersed in an oil bath at 40° C., followed by stirring for 30 minutes. Thereafter, using a dropping funnel, 9.0 g (0.1 mol) of trimethylsilanol was added over 1 hour and, after the addition, the mixture was stirred for additional 1 hour. The content of the flask was transferred to a 200 ml recovery flask, and isopropanol thus formed was distilled off under reduced pressure to obtain a colorless liquid titanium compound (T2).

Analysis of the titanium compound (T2) by FT-IR revealed that an absorption peak of Ti—O—Si (958 cm$^{-1}$) was formed and there was no absorption of silanol (883 cm$^{-1}$), and thus the obtained titanium compound (T2) is triisopropoxy(trimethylsiloxy)titanium.

(Synthesis Example 3) Synthesis of Titanium Compound (T3)

In a three-necked flask having a capacity of 500 ml, 34.0 g (0.1 mol) of tetra-t-butoxytitanium was charged and the flask was immersed in an oil bath at 40° C., followed by stirring for 30 minutes. Thereafter, using a dropping funnel, 9.0 g (0.1 mol) of trimethylsilanol was added over 1 hour and, after the addition, the mixture was stirred for additional 1 hour. The content of the flask was transferred to a 200 ml recovery flask, and t-butanol thus formed was distilled off under reduced pressure to obtain a colorless liquid titanium compound (T3).

Analysis of the titanium compound (T3) by FT-IR revealed that an absorption peak of Ti—O—Si (958 cm$^{-1}$) was formed and there was no absorption of silanol (883 cm$^{-1}$), and thus the obtained titanium compound (T3) is tri-t-butoxy(trimethylsiloxy)titanium.

(Synthesis Example 4) Synthesis of Titanium Compound (T4)

In a three-necked flask having a capacity of 500 ml, 34.0 g (0.1 mol) of tetrabutoxytitanium was charged and the flask was immersed in an oil bath at 40° C., followed by stirring for 30 minutes. Thereafter, using a dropping funnel, 13.3 g (0.1 mol) of triethylsilanol was added over 1 hour and, after the addition, the mixture was stirred for additional 1 hour. The content of the flask was transferred to a 200 ml recovery flask, and butanol thus formed was distilled off under reduced pressure to obtain a colorless liquid titanium compound (T4).

Analysis of the titanium compound (T4) by FT-IR revealed that an absorption peak of Ti—O—Si (958 cm$^{-1}$) was formed and there was no absorption of silanol (883 cm$^{-1}$), and thus the obtained titanium compound (T4) is tributoxy(triethylsiloxy)titanium.

(Synthesis Example 5) Synthesis of Titanium Compound (T5)

In a three-necked flask having a capacity of 500 ml, 34.0 g (0.1 mol) of tetrabutoxytitanium was charged and the flask was immersed in an oil bath at 40° C., followed by stirring for 30 minutes. Thereafter, using a dropping funnel, 18.0 g (0.2 mol) of trimethylsilanol was added over 1 hour and, after the addition, the mixture was stirred for additional 1 hour. The content of the flask was transferred to a 200 ml recovery flask, and butanol thus formed was distilled off under reduced pressure to obtain a colorless liquid titanium compound (T5).

Analysis of the titanium compound (T5) by FT-IR revealed that an absorption peak of Ti—O—Si (958 cm$^{-1}$) was formed and there was no absorption of silanol (883 cm$^{-1}$), and that the obtained titanium compound (T5) is dibutoxybis(trimethylsiloxy)titanium because the absorption peak intensity of Ti—O—Si doubled as compared with the titanium compound (T1).

(Synthesis Example 6) Synthesis of Titanium Compound (T6)

In a three-necked flask having a capacity of 500 ml, 34.0 g (0.1 mol) of tetrabutoxytitanium was charged and the flask was immersed in an oil bath at 40° C., followed by stirring for 30 minutes. Thereafter, using a dropping funnel, 27.1 g (0.3 mol) of trimethylsilanol was added over 1 hour and, after the addition, the mixture was stirred for additional 1 hour. The content of the flask was transferred to a 200 ml recovery flask, and butanol thus formed was distilled off under reduced pressure to obtain a colorless liquid titanium compound (T6).

Analysis of the titanium compound (T6) by FT-IR revealed that an absorption peak of Ti—O—Si (958 cm$^{-1}$) was formed and there was no absorption of silanol (883 cm$^{-1}$), and that the obtained titanium compound (T6) is butoxytris(trimethylsiloxy)titanium) because the absorption peak intensity of Ti—O—Si tripled as compared with the titanium compound (T1).

(Synthesis Example 7) Synthesis of Zirconium Compound (Z1)

In a three-necked flask having a capacity of 500 ml, 38.4 g (0.1 mol) of tetrabutoxyzirconium was charged and the flask was immersed in an oil bath at 40° C., followed by stirring for 30 minutes. Thereafter, using a dropping funnel, 9.0 g (0.1 mol) of trimethylsilanol was added over 1 hour and, after the addition, the mixture was stirred for additional 1 hour. The content of the flask was transferred to a 200 ml recovery flask, and butanol thus formed was distilled off under reduced pressure to obtain a colorless liquid zirconium compound (Z1).

Analysis of the zirconium compound (Z1) by FT-IR revealed that an absorption peak of Zr—O—Si (968 cm$^{-1}$) was formed and there was no absorption of silanol (883 cm$^{-1}$), and thus the obtained zirconium compound (Z1) is tributoxy(trimethylsiloxy)zirconium.

(Synthesis Example 8) Synthesis of Zirconium Compound (Z2)

In a three-necked flask having a capacity of 500 ml, 32.8 g (0.1 mol) of tetrapropoxyzirconium was charged and the flask was immersed in an oil bath at 40° C., followed by stirring for 30 minutes. Thereafter, using a dropping funnel, 9.0 g (0.1 mol) of trimethylsilanol was added over 1 hour and, after the addition, the mixture was stirred for additional 1 hour. The content of the flask was transferred to a 200 ml recovery flask, and propanol thus formed was distilled off under reduced pressure to obtain a colorless liquid zirconium compound (Z2).

Analysis of the zirconium compound (Z2) by FT-IR revealed that an absorption peak of Zr—O—Si (968 cm$^{-1}$) was formed and there was no absorption of silanol (883 cm$^{-1}$), and thus the obtained zirconium compound (Z2) is tripropoxy(trimethylsiloxy)zirconium.

(Synthesis Example 9) Synthesis of Zirconium Compound (Z3)

In a three-necked flask having a capacity of 500 ml, 38.4 g (0.1 mol) of tetrabutoxyzirconium was charged and the flask was immersed in an oil bath at 40° C., followed by stirring for 30 minutes. Thereafter, using a dropping funnel, 18.0 g (0.1 mol) of triethylsilanol was added over 1 hour and, after the addition, the mixture was stirred for additional 1 hour. The content of the flask was transferred to a 200 ml recovery flask, and butanol thus formed was distilled off under reduced pressure to obtain a colorless liquid zirconium compound (Z3).

Analysis of the zirconium compound (Z3) by FT-IR revealed that an absorption peak of Zr—O—Si (968 cm$^{-1}$) was formed and there was no absorption of silanol (883 cm$^{-1}$), and thus the obtained zirconium compound (Z3) is tributoxy(triethylsiloxy)zirconium.

(Synthesis Example 10) Synthesis of Zirconium Compound (Z4)

In a three-necked flask having a capacity of 500 ml, 38.4 g (0.1 mol) of tetrabutoxyzirconium was charged and the flask was immersed in an oil bath at 40° C., followed by stirring for 30 minutes. Thereafter, using a dropping funnel, 18.0 g (0.2 mol) of trimethylsilanol was added over 1 hour and, after the addition, the mixture was stirred for additional 1 hour. The content of the flask was transferred to a 200 ml recovery flask, and butanol thus formed was distilled off under reduced pressure to obtain a colorless liquid zirconium compound (Z4).

Analysis of the zirconium compound (Z4) by FT-IR revealed that an absorption peak of Zr—O—Si (968 cm$^{-1}$) was formed and there was no absorption of silanol (883 cm$^{-1}$), and that the obtained zirconium compound (Z4) is dibutoxybis(trimethylsiloxy)zirconium because the absorption peak intensity of Zr—O—Si doubled as compared with the zirconium compound (Z3).

Synthesis Examples 1 to 10 are collectively shown in Table 1.

TABLE 1

|  |  | Obtained metal compound | $R^4$ | $R^5$ | M | m | n |
|---|---|---|---|---|---|---|---|
| Synthesis Example 1 | Titanium compound (T1) | Tributoxy(trimethylsiloxy)titanium | Methyl | Butyl | Ti | 4 | 1 |
| Synthesis Example 2 | Titanium compound (T2) | Triisopropoxy(trimethylsiloxy)titanium | Methyl | Isopropyl | Ti | 4 | 1 |
| Synthesis Example 3 | Titanium compound (T3) | Tri-t-butoxy(trimethylsiloxy)titanium | Methyl | t-Butyl | Ti | 4 | 1 |
| Synthesis Example 4 | Titanium compound (T4) | Tributoxy(triethylsiloxy)titanium | Ethyl | Butyl | Ti | 4 | 1 |
| Synthesis Example 5 | Titanium compound (T5) | Dibutoxybis(trimethylsiloxy)titanium | Methyl | Butyl | Ti | 4 | 2 |
| Synthesis Example 6 | Titanium compound (T6) | Butoxytris(trimethylsiloxy)titanium | Methyl | Butyl | Ti | 4 | 3 |
| Synthesis Example 7 | Zirconium compound (Z1) | Tributoxy(trimethylsiloxy)zirconium | Methyl | Butyl | Zr | 4 | 1 |
| Synthesis Example 8 | Zirconium compound (Z2) | Tripropoxy(trimethylsiloxy)zirconium | Methyl | Propyl | Zr | 4 | 1 |
| Synthesis Example 9 | Zirconium compound (Z3) | Tributoxy(triethylsiloxy)zirconium | Ethyl | Butyl | Zr | 4 | 1 |
| Synthesis Example 10 | Zirconium compound (Z4) | Dibutoxybis(trimethylsiloxy)zirconium | Methyl | Butyl | Zr | 4 | 2 |

(Synthesis Example 11) Titanium Compound (T1-H1) Solution

In a three-necked flask having a capacity of 500 ml, 35.6 g (0.1 mol) of a titanium compound (T1) and 50.0 g of propylene glycol monomethyl ether acetate (hereinafter abbreviated to PGMEA) as a solvent were charged and the flask was immersed in an oil bath at 40° C., followed by stirring for 30 minutes. Thereafter, 1.8 g (0.1 mol) of water was charged in a dropping funnel for the purpose of hydrolysis, and then added in the flask over 1 hour. During the addition of water, precipitation did not occur in the liquid in the flask, and it was a uniform colorless and transparent solution. After the addition, the mixture was stirred for additional 1 hour.

The content of the flask was transferred to a 200 ml recovery flask and butanol thus formed was distilled off under reduced pressure to obtain a colorless and transparent titanium compound (T1-H1) solution. Analysis of the obtained titanium compound (T1-H1) solution by FT-IR revealed an absorption peak of Ti—O—Si (958 cm$^{-1}$) and an absorption peak of Ti—OH (1,645 cm$^{-1}$ and 3,380 cm$^{-1}$). Therefore, it was estimated that the titanium compound (T1-H1) is dibutoxy(hydroxy)(trimethylsiloxy)titanium.

These results are shown in Table 2.

Synthesis Example 12 to Synthesis Example 25, Comparative Synthesis Example 1 to Comparative Synthesis Example 3

In a 500 ml three-necked flask, titanium compounds and solvents shown in Table 2 were charged, followed by stirring in the same manner as in Synthesis Example 11. Thereafter, water was added in the amount shown in Table 2 in the same manner as in Synthesis Example 11, followed by hydrolysis. Appearance of the flask content liquid during the addition of water is shown in Table 2. In the same manner as in Synthesis Example 11, alcohol as a by-product was distilled off under reduced pressure. The results of analysis by FT-IR are shown in Table 2.

Regarding Comparative Synthesis Examples 1 to 3, when water was added, white precipitation occurred instantaneously. The reason is considered that tetrahydroxy titanium was formed because of high hydrolysis rate of titanium alkoxide. Therefore, it is estimated that tetrahydroxytitanium thus formed aggregated and became insoluble in the solvent.

The content of the flask was transferred to a 200 ml recovery flask and butanol thus formed was distilled off under reduced pressure to obtain a colorless and transparent zirconium compound (Z1-H1) solution. Analysis of the obtained zirconium compound (Z1-H1) solution by FT-IR revealed an absorption peak of Zr—O—Si (968 cm$^{-1}$) and an absorption peak of Zr—OH (1,600 cm$^{-1}$ and 3,410 cm$^{-1}$). Therefore, it was estimated that the zirconium compound (Z1-H1) is dibutoxy(hydroxy)(trimethylsiloxy)zirconium.

These results are shown in Table 3.

TABLE 2

| | | Charging | | | | Amount of water added | Appearance of solution | Estimated structure |
|---|---|---|---|---|---|---|---|---|
| | | Metal compound | | Solvent | | | | |
| | | Type | Amount | Type | Amount | | | |
| Synthesis Example 11 | Titanium compound (T1-H1) solution | Titanium compound (T1) | 35.6 g (0.1 mol) | PGMEA | 50 g | 1.8 g (0.1 mol) | Transparent | Dibutoxy(hydroxy)(trimethylsiloxy)titanium |
| Synthesis Example 12 | Titanium compound (T1-H2) solution | Titanium compound (T1) | 35.6 g (0.1 mol) | PGMEA | 50 g | 3.6 g (0.2 mol) | Transparent | Butoxy(dihydroxy)(trimethylsiloxy)titanium |
| Synthesis Example 13 | Titanium compound (T1-H3) solution | Titanium compound (T1) | 35.6 g (0.1 mol) | PGMEA | 50 g | 5.4 g (0.3 mol) | Transparent | Trihydroxy(trimethylsiloxy)titanium |
| Synthesis Example 14 | Titanium compound (T2-H1) solution | Titanium compound (T2) | 31.4 g (0.1 mol) | PGMEA | 50 g | 1.8 g (0.1 mol) | Transparent | Di(isopropoxy)(hydroxy)(trimethylsiloxy)titanium |
| Synthesis Example 15 | Titanium compound (T2-H2) solution | Titanium compound (T2) | 31.4 g (0.1 mol) | PGMEA | 50 g | 3.6 g (0.2 mol) | Transparent | (Isopropoxy)(dihydroxy)(trimethylsiloxy)titanium |
| Synthesis Example 16 | Titanium compound (T2-H3) solution | Titanium compound (T2) | 31.4 g (0.1 mol) | PGMEA | 50 g | 5.4 g (0.3 mol) | Transparent | Trihydroxy(trimethylsiloxy)titanium |
| Synthesis Example 17 | Titanium compound (T3-H1) solution | Titanium compound (T3) | 35.6 g (0.1 mol) | PGMEA | 50 g | 1.8 g (0.1 mol) | Transparent | Di(t-butoxy)(hydroxy)(trimethylsiloxy)titanium |
| Synthesis Example 18 | Titanium compound (T3-H2) solution | Titanium compound (T3) | 35.6 g (0.1 mol) | PGMEA | 50 g | 3.6 g (0.2 mol) | Transparent | T-butoxy(dihydroxy)(trimethylsiloxy)titanium |
| Synthesis Example 19 | Titanium compound (T3-H3) solution | Titanium compound (T3) | 35.6 g (0.1 mol) | PGMEA | 50 g | 5.4 g (0.3 mol) | Transparent | Trihydroxy(trimethylsiloxy)titanium |
| Synthesis Example 20 | Titanium compound (T4-H1) solution | Titanium compound (T4) | 39.8 g (0.1 mol) | PGMEA | 50 g | 1.8 g (0.1 mol) | Transparent | Dibutoxy(hydroxy)(triethylsiloxy)titanium |
| Synthesis Example 21 | Titanium compound (T4-H2) solution | Titanium compound (T4) | 39.8 g (0.1 mol) | PGMEA | 50 g | 3.6 g (0.2 mol) | Transparent | Butoxy(dihydroxy)(triethylsiloxy)titanium |
| Synthesis Example 22 | Titanium compound (T4-H3) solution | Titanium compound (T4) | 39.8 g (0.1 mol) | PGMEA | 50 g | 5.4 g (0.3 mol) | Transparent | Trihydroxy(triethylsiloxy)titanium |
| Synthesis Example 23 | Titanium compound (T5-H1) solution | Titanium compound (T5) | 37.2 g (0.1 mol) | PGMEA | 50 g | 1.8 g (0.1 mol) | Transparent | Butoxy(hydroxy)bis(trimethylsiloxy)titanium |
| Synthesis Example 24 | Titanium compound (T5-H2) solution | Titanium compound (T5) | 37.2 g (0.1 mol) | PGMEA | 50 g | 3.6 g (0.2 mol) | Transparent | Dihydroxybis(trimethylsiloxy)titanium |
| Synthesis Example 25 | Titanium compound (T6-H1) solution | Titanium compound (T6) | 38.9 g (0.1 mol) | PGMEA | 50 g | 1.8 g (0.1 mol) | Transparent | Hydroxytris(trimethylsiloxy)titanium |
| Comparative Synthesis Example 1 | Hydrolyzate of tetrabutoxytitanium | Tetrabutoxytitanium | 34.0 g (0.1 mol) | PGMEA | 50 g | 1.8 g (0.1 mol) | White solid precipitation | Mixture of tetrahydroxytitanium and tetrabutoxytitanium |
| Comparative Synthesis Example 2 | Hydrolyzate of tetraisopropoxytitanium | Tetraisopropoxytitanium | 28.4 g (0.1 mol) | PGMEA | 50 g | 1.8 g (0.1 mol) | White solid precipitation | Mixture of tetrahydroxytitanium and tetraisopropoxytitanium |
| Comparative Synthesis Example 3 | Hydrolyzate of tetra-t-butoxytitanium | Tetra-t-butoxytitanium | 34.0 g (0.1 mol) | PGMEA | 50 g | 1.8 g (0.1 mol) | White solid precipitation | Mixture of tetrahydroxytitanium and tetra(t-butoxy)titanium |

(Synthesis Example 26) Zirconium Compound (Z1-H1) Solution

In a 500 ml three-necked flask, 40.0 g (0.1 mol) of the zirconium compound (Z1) and 50.0 g of PGMEA as a solvent were charged and the flask was immersed in an oil bath at 40° C., followed by stirring for 30 minutes. Thereafter, 1.8 g (0.1 mol) of water was charged in a dropping funnel for the purpose of hydrolysis, and then added in the flask over 1 hour. During the addition of water, precipitation did not occur in the liquid in the flask, and it was a uniform colorless and transparent solution. After the addition, the mixture was stirred for additional 1 hour.

Synthesis Example 27 to Synthesis Example 36, Comparative Synthesis Example 4 to Comparative Synthesis Example 5

In a 500 ml three-necked flask, zirconium compounds and solvents shown in Table 3 were charged, followed by stirring in the same manner as in Synthesis Example 26. Thereafter, water was added in the amount shown in Table 3 in the same manner as in Synthesis Example 26, followed by hydrolysis. Appearance of the flask content liquid during the addition of water is shown in Table 3. In the same manner as in Synthesis Example 26, alcohol as a by-product was distilled off under reduced pressure. The results of analysis by FT-IR are shown in Table 3.

Regarding Comparative Synthesis Examples 4 and 5, when water was added, white precipitation occurred instantaneously. The reason is considered that tetrahydroxy zirconium was formed because of high hydrolysis rate of zirconium alkoxide. Therefore, it is estimated that tetrahydroxyzirconium thus formed aggregated and became insoluble in the solvent.

concentration of 0.2% by weight, and the solution thus obtained was used as a sample solution. A porous gel column (each one of TSK gel α-M, α-3000, manufactured by Tosoh Corporation) was packed with the eluent at a flow rate of 0.5 mL/min, and 0.2 mL of the sample solution was injected into the column. The column eluate was detected by a differential refractive index detector (Model RI-201, manufactured by Showa Denko K.K.) and the elution time was analyzed to determine the weight average molecular weight (Mw).

TABLE 3

| | Charging | | | | Amount of | | |
|---|---|---|---|---|---|---|---|
| | Metal compound | | Solvent | | water | Appearance of | |
| | Type | Amount | Type | Amount | added | solution | Estimated structure |
| Synthesis Example 26 | Zirconium compound (Z1-H1) solution | Zirconium compound (Z1) | 40.0 g (0.1 mol) | PGMEA | 50 g | 1.8 g (0.1 mol) | Transparent | Di(butoxy)(hydroxy)(tri-methylsiloxy)zirconium |
| Synthesis Example 27 | Zirconium compound (Z1-H2) solution | Zirconium compound (Z1) | 40.0 g (0.1 mol) | PGMEA | 50 g | 3.6 g (0.2 mol) | Transparent | Butoxy(dihydroxy)(tri-methylsiloxy)zirconium |
| Synthesis Example 28 | Zirconium compound (Z1-H3) solution | Zirconium compound (Z1) | 40.0 g (0.1 mol) | PGMEA | 50 g | 5.4 g (0.3 mol) | Transparent | Trihydroxy(tri-methylsiloxy)zirconium |
| Synthesis Example 29 | Zirconium compound (Z2-H1) solution | Zirconium compound (Z2) | 31.4 g (0.1 mol) | PGMEA | 50 g | 1.8 g (0.1 mol) | Transparent | Di(propoxy)(hydroxy)(tri-methylsiloxy)zirconium |
| Synthesis Example 30 | Zirconium compound (Z2-H2) solution | Zirconium compound (Z2) | 31.4 g (0.1 mol) | PGMEA | 50 g | 3.6 g (0.2 mol) | Transparent | (Propoxy)(dihydroxy)(tri-methylsiloxy)zirconium |
| Synthesis Example 31 | Zirconium compound (Z2-H3) solution | Zirconium compound (Z2) | 31.4 g (0.1 mol) | PGMEA | 50 g | 5.4 g (0.3 mol) | Transparent | Trihydroxy(tri-methylsiloxy)zirconium |
| Synthesis Example 32 | Zirconium compound (Z3-H1) solution | Zirconium compound (Z3) | 44.1 g (0.1 mol) | PGMEA | 50 g | 1.8 g (0.1 mol) | Transparent | Di(butoxy)(hydroxy)(tri-ethylsiloxy)zirconium |
| Synthesis Example 33 | Zirconium compound (Z3-H2) solution | Zirconium compound (Z3) | 44.1 g (0.1 mol) | PGMEA | 50 g | 3.6 g (0.2 mol) | Transparent | Butoxy(dihydroxy)(tri-ethylsiloxy)zirconium |
| Synthesis Example 34 | Zirconium compound (Z3-H3) solution | Zirconium compound (Z3) | 44.1 g (0.1 mol) | PGMEA | 50 g | 5.4 g (0.3 mol) | Transparent | Trihydroxy(tri-ethylsiloxy)zirconium |
| Synthesis Example 35 | Zirconium compound (Z4-H1) solution | Zirconium compound (Z4) | 41.6 g (0.1 mol) | PGMEA | 50 g | 1.8 g (0.1 mol) | Transparent | Butoxy(hydroxy)di(tri-methylsiloxy)zirconium |
| Synthesis Example 36 | Zirconium compound (Z4-H2) solution | Zirconium compound (Z4) | 41.6 g (0.1 mol) | PGMEA | 50 g | 3.6 g (0.2 mol) | Transparent | Dihydroxybis(tri-methylsiloxy)zirconium |
| Comparative Synthesis Example 4 | Hydrolyzate of tetrabutoxy-zirconium | Tetrabutoxy-zirconium | 38.4 g (0.1 mol) | PGMEA | 50 g | 1.8 g (0.1 mol) | White solid precipitation | Mixture of tetrahydroxy-zirconium and tetrabutoxyzirconium |
| Comparative Synthesis Example 5 | Tetrapropoxy-zirconium | Tetrapropoxy-zirconium | 32.8 g (0.1 mol) | PGMEA | 50 g | 1.8 g (0.1 mol) | White solid precipitation | Mixture of tetrahydroxy-zirconium and tetrapropoxyzirconium |

In each Example, the solid content concentration of a polymetalloxane solution was determined by weighing 1.0 g of the polymetalloxane solution in an aluminum cup, heating the polymetalloxane solution at 250° C. for 30 minutes using a hot plate to vaporize the liquid component, and weighing the solid component remaining in the aluminum cup after heating.

Analysis by FT-IR was carried out by the following method. First, only a silicon wafer was measured using a Fourier transform infrared spectrometer (FT720, manufactured by Shimadzu Corporation) and was used as a baseline. Subsequently, the polymetalloxane solution was dropped onto a silicon wafer, followed by spin coating at an arbitrary rotational speed, followed by vacuum drying to fabricate a measurement sample. An absorbance of the polymetalloxane was calculated from the difference between the absorbance of the measurement sample and the absorbance of the baseline, and an absorption peak was read.

The weight average molecular weight (Mw) was determined by the following method. Lithium chloride was dissolved in N-methyl-2-pyrrolidone to prepare a 0.02 M lithium chloride/N-methyl-2-pyrrolidone solution as an eluent. A polymetalloxane was dissolved in the eluent in the Example 1 Synthesis of Polymetalloxane (TP-1)

The titanium compound (T1) (35.6 g (0.1 mol)) and 50.0 g of propylene glycol monomethyl ether acetate (hereinafter abbreviated to PGMEA) as a solvent were mixed to obtain a solution 1. Water (1.8 g (0.1 mol)), 50.0 g of isopropyl alcohol (hereinafter abbreviated to IPA) as a diluting solvent for water, and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-1) solution.

Analysis of the polymetalloxane (TP-1) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-1) was 6,000 in terms of polystyrene.

Example 2 Synthesis of Polymetalloxane (TP-2)

The titanium compound (T1) (35.6 g (0.1 mol)) and 50.0 g of PGMEA as a solvent were mixed to obtain a solution 1. Water (3.6 g (0.2 mol)), 50.0 g of IPA as a diluting solvent for water, and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-2) solution.

Analysis of the polymetalloxane (TP-2) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-2) was 21,000 in terms of polystyrene.

Example 3 Synthesis of Polymetalloxane (TP-3)

The titanium compound (T1) (35.6 g (0.1 mol)) and 50.0 g of PGMEA as a solvent were mixed to obtain a solution 1. Water (3.6 g (0.2 mol)), 50.0 g of IPA as a diluting solvent for water, and 1.3 g (0.01 mol) of diisobutylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-3) solution.

Analysis of the polymetalloxane (TP-3) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-3) was 25,000 in terms of polystyrene.

Example 4 Synthesis of Polymetalloxane (TP-4)

The titanium compound (T1) (35.6 g (0.1 mol)) and 50.0 g of PGMEA as a solvent were mixed to obtain a solution 1. Water (3.6 g (0.2 mol)) and 50.0 g of IPA as a diluting solvent for water were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-4) solution.

Analysis of the polymetalloxane (TP-4) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-4) was 6,000 in terms of polystyrene.

Example 5 Synthesis of Polymetalloxane (TP-5)

The titanium compound (T1) (35.6 g (0.1 mol)) and 50.0 g of PGMEA as a solvent were mixed to obtain a solution 1. Water (5.4 g (0.3 mol)), 50.0 g of IPA as a diluting solvent for water, and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-5) solution.

Analysis of the polymetalloxane (TP-5) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-5) was 44,000 in terms of polystyrene.

Example 6 Synthesis of Polymetalloxane (TP-6)

The titanium compound (T1) (35.6 g (0.1 mol)) and 50.0 g of PGMEA as a solvent were mixed to obtain a solution 1. Water (5.4 g (0.3 mol)), 50.0 g of IPA as a diluting solvent for water, and 1.3 g (0.01 mol) of diisobutylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-6) solution.

Analysis of the polymetalloxane (TP-6) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-6) was 25,000 in terms of polystyrene.

Example 7 Synthesis of Polymetalloxane (TP-7)

The titanium compound (T2) (31.4 g (0.1 mol)) and 50.0 g of PGMEA as a solvent were mixed to obtain a solution 1. Water (5.4 g (0.3 mol)), 50.0 g of IPA as a diluting solvent for water, and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-7) solution.

Analysis of the polymetalloxane (TP-7) solution by FT-IR revealed that an absorption peak of Ti—O—Si (958 cm$^{-1}$)

was observed, and thus the polymetalloxane is a polymetalloxane having a trimethylsiloxy group.

The weight average molecular weight (Mw) of the polymetalloxane (TP-7) was 46,000 in terms of polystyrene.

Example 8 Synthesis of Polymetalloxane (TP-8)

The titanium compound (T4) (39.8 g (0.1 mol)) and 50.0 g of PGMEA as a solvent were mixed to obtain a solution 1. Water (5.4 g (0.3 mol)), 50.0 g of IPA as a diluting solvent for water, and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-8) solution.

Analysis of the polymetalloxane (TP-8) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-8) was 28,000 in terms of polystyrene.

Example 9 Synthesis of Polymetalloxane (TP-9)

The titanium compound (T5) (37.2 g (0.1 mol)) and 50.0 g of PGMEA as a solvent were mixed to obtain a solution 1. Water (3.6 g (0.2 mol)), 50.0 g of IPA as a diluting solvent for water, and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-9) solution.

Analysis of the polymetalloxane (TP-9) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-9) was 18,000 in terms of polystyrene.

Example 10 Synthesis of Polymetalloxane (TP-10)

A titanium compound (T2-H3) solution (68.81 g) (composed of 18.81 g (0.1 mol) of trihydroxy(trimethylsiloxy) titanium) and 50.0 g of PGMEA) was weighed and this solution was used as a solution 1. IPA (50.0 g) as a diluting solvent for water and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and water as a by-product were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-10) solution.

Analysis of the polymetalloxane (TP-10) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-10) was 48,000 in terms of polystyrene.

Example 11 Synthesis of Polymetalloxane (TP-11)

A titanium compound (T2-H2) solution (73.02 g) (composed of 18.81 g (0.1 mol) of (isopropoxy)(dihydroxy)(trimethylsiloxy)titanium) and 50.0 g of PGMEA) was weighed and this solution was used as a solution 1. Water (1.8 g (0.1 mol)), 50.0 g of IPA as a diluting solvent for water, and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and water were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (TP-11) solution.

Analysis of the polymetalloxane (TP-11) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-11) was 47,000 in terms of polystyrene.

Example 12 Synthesis of Polymetalloxane (TP-12)

In the same manner as in Example 7, except that PGMEA as the solvent of Example 7 was changed to 1,2-diethoxyethane, synthesis and adjustment of the solid component were performed to obtain a polymetalloxane (TP-12) solution. The appearance of the obtained polymetalloxane (TP-12) solution was pale yellow transparent.

Analysis of the polymetalloxane (TP-12) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-12) was 49,000 in terms of polystyrene.

Example 13 Synthesis of Polymetalloxane (TP-13)

In the same manner as in Example 7, except that PGMEA as the solvent of Example 7 was changed to 2,6-dimethyl-4-heptanone, synthesis and adjustment of the solid component were performed to obtain a polymetalloxane (TP-13) solution. The appearance of the obtained polymetalloxane (TP-13) solution was pale yellow transparent.

Analysis of the polymetalloxane (TP-13) solution by FT-IR revealed that an absorption peak of Ti—O—Si (958 cm$^{-1}$) was observed, and thus the polymetalloxane is a polymetalloxane having a trimethylsiloxy group.

The weight average molecular weight (Mw) of the polymetalloxane (TP-13) was 46,000 in terms of polystyrene.

Example 14 Synthesis of Polymetalloxane (ZP-1)

The zirconium compound (Z-1) (40.0 g (0.1 mol)) and 50.0 g of PGMEA as a solvent were mixed to obtain a solution 1. Water (5.4 g (0.3 mol)), 50.0 g of IPA as a diluting solvent for water, and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (ZP-1) solution.

Analysis of the polymetalloxane (ZP-1) solution by FT-IR revealed that an absorption peak of Zr—O—Si (968 cm$^{-1}$) was observed, and thus the polymetalloxane is a polymetalloxane having a trimethylsiloxy group.

The weight average molecular weight (Mw) of the polymetalloxane (ZP-1) was 45,000 in terms of polystyrene.

Example 15 Synthesis of Polymetalloxane (ZP-2)

The zirconium compound (Z-4) (41.6 g (0.1 mol)) and 50.0 g of PGMEA as a solvent were mixed to obtain a solution 1. Water (3.6 g (0.2 mol)), 50.0 g of IPA as a diluting solvent for water, and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, butanol and water as by-products were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (ZP-2) solution.

Analysis of the polymetalloxane (ZP-2) solution by FT-IR revealed that an absorption peak of Zr—O—Si (968 cm$^{-1}$) was observed, and thus the polymetalloxane is a polymetalloxane having a trimethylsiloxy group.

The weight average molecular weight (Mw) of the polymetalloxane (ZP-2) was 19,000 in terms of polystyrene.

Example 16 Synthesis of Polymetalloxane (ZP-3)

A zirconium compound (Z1-H3) solution (73.1 g) (composed of g (0.1 mol) of trihydroxy(trimethylsiloxy)zirconium) and 50.0 g of PGMEA) was weighed and this solution was used as a solution 1. IPA (50.0 g) as a diluting solvent for water and 2.2 g (0.01 mol) of tributylamine as a polymerization catalyst were mixed to obtain a solution 2.

In a three-necked flask having a capacity of 500 ml, the entire amount of the solution 1 was charged and the flask was immersed in an oil bath at 40° C., followed by stirring for 30 minutes. Thereafter, the entire amount of the solution 2 was charged in a dropping funnel for the purpose of hydrolysis, and then added in the flask over 1 hour. During the addition of the solution 2, precipitation did not occur in the liquid in the flask, and it was a uniform colorless and transparent solution. After the addition, the mixture was stirred for additional 1 hour to obtain a metal compound containing a hydroxyl group. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, IPA and water as a by-product were distilled. During heating with stirring, precipitation did not occur in the liquid in the flask, and it was a uniform transparent solution.

After completion of the heating, the liquid in the flask was cooled to room temperature to obtain a polymetalloxane solution. The appearance of the obtained polymetalloxane solution was pale yellow transparent.

The solid component concentration of the obtained polymetalloxane solution was determined, and then PGMEA was added such that the solid component concentration became 20% by weight to obtain a polymetalloxane (ZP-3) solution.

Analysis of the polymetalloxane (ZP-3) solution by FT-IR revealed that an absorption peak of Zr—O—Si (968 cm$^{-1}$) was observed, and thus the polymetalloxane is a polymetalloxane having a trimethylsiloxy group.

The weight average molecular weight (Mw) of the polymetalloxane (ZP-3) was 46,000 in terms of polystyrene.

Examples 1 to 16 are collectively shown in Table 4.

TABLE 4

| | | Solution 1 | | | | | | | Solvent | |
|---|---|---|---|---|---|---|---|---|---|---|
| | | Compound represented by general formula (2) | | | | | | | Addition | |
| | | Type | M | R$^4$ | n | R$^5$ | m − n | Amount | Type | amount |
| Example 1 | Polymetalloxane (TP-1) solution | Titanium compound (T1) | Ti | Methyl | 1 | Butyl | 3 | 35.6 g (0.1 mol) | PGMEA | 50.0 g |
| Example 2 | Polymetalloxane (TP-2) solution | | Ti | Methyl | 1 | Butyl | 3 | 35.6 g (0.1 mol) | PGMEA | 50.0 g |
| Example 3 | Polymetalloxane (TP-3) solution | | Ti | Methyl | 1 | Butyl | 3 | 35.6 g (0.1 mol) | PGMEA | 50.0 g |
| Example 4 | Polymetalloxane (TP-4) solution | | Ti | Methyl | 1 | Butyl | 3 | 35.6 g (0.1 mol) | PGMEA | 50.0 g |
| Example 5 | Polymetalloxane (TP-5) solution | | Ti | Methyl | 1 | Butyl | 3 | 35.6 g (0.1 mol) | PGMEA | 50.0 g |
| Example 6 | Polymetalloxane (TP-6) solution | | Ti | Methyl | 1 | Butyl | 3 | 35.6 g (0.1 mol) | PGMEA | 50.0 g |
| Example 7 | Polymetalloxane (TP-7) solution | Titanium compound (T2) | Ti | Methyl | 1 | Isopropyl | 3 | 31.4 g (0.1 mol) | PGMEA | 50.0 g |
| Example 8 | Polymetalloxane (TP-8) solution | Titanium compound (T4) | Ti | Ethyl | 1 | Butyl | 3 | 39.8 g (0.1 mol) | PGMEA | 50.0 g |
| Example 9 | Polymetalloxane (TP-9) solution | Titanium compound (T5) | Ti | Methyl | 2 | Butyl | 2 | 37.2 g (0.1 mol) | PGMEA | 50.0 g |
| Example 10 | Polymetalloxane (TP-10) solution | Titanium compound (T2-H3) | Ti | Methyl | 1 | Hydrogen | 3 | 18.81 g (0.1 mol) | PGMEA | 50.0 g |
| Example 11 | Polymetalloxane (TP-11) solution | Titanium compound (T2-H2) | Ti | Methyl | 1 | Isopropyl, Hydrogen | 3 | 23.02 g (0.1 mol) | PGMEA | 50.0 g |
| Example 12 | Polymetalloxane (TP-12) solution | Titanium compound (T2) | Ti | Methyl | 1 | Isopropyl | 3 | 31.4 g (0.1 mol) | Diethoxyethane | 50.0 g |
| Example 13 | Polymetalloxane (TP-13) solution | Titanium compound (T2) | Ti | Methyl | 1 | Isopropyl | 3 | 31.4 g (0.1 mol) | 2,6-Dimethyl-4,-heptanone | 50.0 g |

TABLE 4-continued

| | | | | | | | | | | |
|---|---|---|---|---|---|---|---|---|---|---|
| Example 14 | Polymetalloxane (ZP-1) solution | Zirconium compound (Z1) | Zr | Methyl | 1 | Butoxy | 3 | 40.0 g (0.1 mol) | PGMEA | 50.0 g |
| Example 15 | Polymetalloxane (ZP-2) solution | Zirconium compound (Z4) | Zr | Methyl | 2 | Butoxy | 2 | 41.6 g (0.1 mol) | PGMEA | 50.0 g |
| Example 16 | Polymetalloxane (ZP-3) solution | Zirconium compound (Z1-H3) | Zr | Methyl | 1 | Hydrogen | 3 | 23.1 g (0.1 mol) | PGMEA | 50.0 g |

| | Solution 2 | | | Weight results | |
|---|---|---|---|---|---|
| | Water | Diluting solvent for water | Polymerization catalyst | Appearance of solution | Weight average molecular weight |
| Example 1 | 1.8 g (0.1 mol) | IPA 50.0 g | Tributylamine 2.2 g (0.01 mol) | Pale yellow transparent | 6,000 |
| Example 2 | 3.6 g (0.2 mol) | IPA 50.0 g | Tributylamine 2.2 g (0.01 mol) | Pale yellow transparent | 21,000 |
| Example 3 | 3.6 g (0.2 mol) | IPA 50.0 g | Diisobutylamine 2.2 g (0.01 mol) | Pale yellow transparent | 25,000 |
| Example 4 | 3.6 g (0.2 mol) | IPA 50.0 g | None | Pale yellow transparent | 6,000 |
| Example 5 | 5.4 g (0.3 mol) | IPA 50.0 g | Tributylamine 2.2 g (0.01 mol) | Pale yellow transparent | 44,000 |
| Example 6 | 5.4 g (0.3 mol) | IPA 50.0 g | Diisobutylamine 2.2 g (0.01 mol) | Pale yellow transparent | 19,0000 |
| Example 7 | 5.4 g (0.3 mol) | IPA 50.0 g | Tributylamine 2.2 g (0.01 mol) | Pale yellow transparent | 46,000 |
| Example 8 | 5.4 g (0.3 mol) | IPA 50.0 g | Tributylamine 2.2 g (0.01 mol) | Pale yellow transparent | 28,000 |
| Example 9 | 3.6 g (0.2 mol) | IPA 50.0 g | Tributylamine 2.2 g (0.01 mol) | Pale yellow transparent | 18,000 |
| Example 10 | 0 g | IPA 50.0 g | Tributylamine 2.2 g (0.01 mol) | Pale yellow transparent | 48,000 |
| Example 11 | 1.8 g (0.1 mol) | IPA 50.0 g | Tributylamine 2.2 g (0.01 mol) | Pale yellow transparent | 47,000 |
| Example 12 | 5.4 g (0.3 mol) | IPA 50.0 g | Tributylamine 2.2 g (0.01 mol) | Pale yellow transparent | 49,000 |
| Example 13 | 5.4 g (0.3 mol) | IPA 50.0 g | Tributylamine 2.2 g (0.01 mol) | Pale yellow transparent | 46,000 |
| Example 14 | 5.4 g (0.3 mol) | IPA 50.0 g | Tributylamine 2.2 g (0.01 mol) | Pale yellow transparent | 45,000 |
| Example 15 | 5.4 g (0.3 mol) | IPA 50.0 g | Tributylamine 2.2 g (0.01 mol) | Pale yellow transparent | 19,000 |
| Example 16 | 5.4 g (0.3 mol) | IPA 50.0 g | Tributylamine 2.2 g (0.01 mol) | Pale yellow transparent | 46,000 |

(Comparative Synthesis Example 6) Synthesis of Polymetalloxane (TP-14)

In a three-necked flask having a capacity of 500 ml, 34.0 g (0.1 mol) of tetrabutoxytitanium was charged and the flask was immersed in an oil bath at 75° C., followed by stirring for 30 minutes (internal temperature was 70° C.). Thereafter, for the purpose of hydrolysis, a mixed solution of 3.1 g (0.17 mol) of water and 50 g of butanol was added over 1 hour by a dropping funnel. During the addition, the temperature was raised to 90° C. and the reaction was aged by holding with stirring for 1 hour.

The content of the flask was transferred to a 200 ml recovery flask, and butanol thus formed was distilled off under reduced pressure to obtain a white solid polymetalloxane (TP-10).

Since the polymetalloxane (TP-14) was not dissolved in PGMEA, the polymetalloxane was dissolved in tetrahydrofuran and adjusted such that the solid component concentration became 20% by weight.

The weight average molecular weight (Mw) of the polymetalloxane (TP-14) was 1,700 in terms of polystyrene.

(Comparative Synthesis Example 7) Synthesis of Polymetalloxane (TP-15)

In a three-necked flask having a capacity of 500 ml, 34.0 g (0.1 mol) of tetrabutoxytitanium and 100 g of ethanol as a solvent were charged and the flask was immersed in an oil bath at 40° C., followed by stirring for 30 minutes. Thereafter, for the purpose of hydrolysis, a mixed solution of 2.7 g (0.15 mol) of water, 0.25 g (0.002 mol) of t-butylhydrazine hydrochloride, and 50 g of ethanol was charged in a dropping funnel and then added in the flask over 1 hour. After the addition, 50 g of PGMEA was added, followed by stirring for additional 1 hour. Thereafter, for the purpose of polycondensation, the oil bath was heated to 140° C. over 30 minutes. One hour after starting of temperature rise, the internal temperature of the solution reached 100° C., and the mixture was heated with stirring for 2 hours (internal temperature was 100 to 130° C.). During the reaction, butanol and water as by-products were distilled.

The solid component concentration of the obtained polymetalloxane solution was determined, and then PGMEA was added such that the solid component concentration became 20% by weight to obtain a polymetalloxane (TP-15) solution.

The weight average molecular weight (Mw) of the polymetalloxane (TP-15) was 8,000 in terms of polystyrene.

(Comparative Synthesis Example 8) Synthesis of Polymetalloxane (SP-1)

In a three-necked flask having a capacity of 500 ml, 20.9 g (0.07 mol) of 2-anthracenyltrimethoxysilane, 6.8 g (0.03 mol) of 4-hydroxybenzyltrimethoxysilane, and 50.0 g of PGMEA as a solvent were charged and, while stirring, a mixed solution of 5.4 g (0.3 mol) of water and 0.2 g of phosphoric acid was added over 1 hour by a dropping funnel for the purpose of hydrolysis. Thereafter, the flask was immersed in an oil bath at 40° C., followed by stirring for 60 minutes and further heating of the oil bath to 120° C. over 30 minutes. One hour after starting of temperature rise, the internal temperature of the solution reached 100° C., and the mixture was heated with stirring for 2 hours (internal temperature was 100 to 110° C.). During the reaction, methanol and water as by-products were distilled.

The solid component concentration of the obtained polymetalloxane solution was determined, and then PGMEA was added such that the solid component concentration became 20% by weight to obtain a polysiloxane (SP-1) solution. The weight average molecular weight (Mw) of the polysiloxane (SP-01) was 3,000 in terms of polystyrene.

(Comparative Synthesis Example 9) Synthesis of Metal Compound Particle-Containing Polysiloxane (SP-2)

A three-necked flask having a capacity of 500 ml was charged with 4.1 g (0.03 mol) of methyltrimethoxysilane, 13.9 g (0.07 mol) of phenyltrimethoxysilane, 315 g of "Optolake TR-527" (trade name, manufactured by Catalyst Chemical Industry Co., Ltd., composition: 20% by weight of titanium oxide particles and 80% by weight of methanol) having a number average particle system of 15 nm, and 50.0 g of PGMEA as a solvent, and a mixed solution of 5.4 g (0.3 mol) of water and 0.2 g of phosphoric acid was added over 1 hour by a dropping funnel for the purpose of hydrolysis while stirring. Thereafter, the flask was immersed in an oil bath at 40° C., followed by stirring for 60 minutes and further heating the oil bath to 120° C. over 30 minutes. One hour after starting of temperature rise, the internal temperature of the solution reached 100° C., and the mixture was heated with stirring for 2 hours (internal temperature was 100 to 110° C.). During the reaction, methanol and water as by-products were distilled.

The solid component concentration of the obtained metal compound particle-containing polymetalloxane solution was determined, and then PGMEA was added such that the solid component concentration became 20% by weight to obtain a metal compound particle-containing polysiloxane (SP-2) solution.

Example 17

(1) Preparation of Cured Film

A polymetalloxane (TP-1) solution was spin-coated on a 4-inch silicon wafer and a Tempax glass plate using a spin coater (1H-360S, manufactured by Mikasa Corporation) and heated at 100° C. for 3 minutes using a hot plate (SCW-636, manufactured by Dainippon Screen Mfg. Co., Ltd.) to form a prebakes film. Thereafter, the film was cured by using a hot plate at 300° C. for 5 minutes to prepare a cured film each having a film thicknesses of 0.3 μm and 0.5 μm. The film thickness was measured using a spectroscopic reflectometer (Lambda Ace STM602, manufactured by Dainippon Screen Mfg. Co., Ltd.).

(2) Evaluation of Crack Resistance of Cured Film

The crack resistance of the cured film obtained in (1) was evaluated in the following 5 ranks. Ranks 4 or more were rated "pass".

5: Cracks are not observed by optical microscope observation (magnification: 5 times)
4: Cracks are slightly observed by optical microscope observation (magnification: 5 times)
3: Cracks are clearly observed by optical microscope observation (magnification: 5 times)
2: Cracks are slightly observed by normal visual observation
1: Cracks are clearly observed by normal visual observation.

(3) Measurement of Refractive Index of Cured Film

With respect to the cured film having a thickness of 0.3 μm formed on a silicon wafer in (1), the temperature during measurement was set at 22° C., and the polarization state change of the reflected light from the cured film was measured using a spectroscopic ellipsometer (FE5000, manufactured by Otsuka Electronics Co., Ltd.) to obtain a phase difference with the incident light and a spectrum of an amplitude reflectance. By fitting the dielectric function of the calculation model such that it approaches the obtained spectrum, a refractive index spectrum was obtained. By reading the refractive index value at a wavelength of 550 nm from the refractive index spectrum, the value was regarded as the refractive index of the cured film.

(4) Measurement of Light Transmittance of Cured Film

Using a spectrophotometer (MultiSpec-1500, manufactured by Shimadzu Corporation), an ultraviolet-visible absorption spectrum of a Tempax glass plate was measured, and this spectrum was used as a reference. Subsequently, the ultraviolet-visible absorption spectrum of the cured film having a thickness of 0.3 μm formed on the Tempax glass plate in (1) was measured, and the ultraviolet-visible absorption spectrum of the cured film was calculated from the difference from the reference. Using the obtained ultraviolet-visible absorption spectrum and film thickness, the light transmittance per 1 μm of the film thickness at a wavelength of 400 nm of the cured film was calculated.

These results are shown in Table 5.

Examples 18 to 32, Comparative Examples 1 to 4

With respect to the solutions shown in Table 5, in the same manner as in Example 17, (1) formation of cured film, (2) crack resistance evaluation of cured film, (3) measurement of refractive index of cured film, and (4) measurement of transmittance of cured film were performed. The evaluation results are shown in Table 5.

Regarding Comparative Example 1 and Comparative Example 2, when a cured film was formed, cracks occurred and a homogeneous film could not be obtained. The reason is considered that, because of the polymetalloxane in which a large amount of alkoxy groups remain, an alkoxy group is hydrolyzed by moisture in the air during formation of the coating film, thus causing elimination and an increase in shrinkage stress, leading to crack generation.

Example 33

A polymetalloxane (TP-5) solution (3.5 g (weight of solid component: 0.7 g)) and 1.0 g (weight of solid component: 0.3 g) of "Optrake TR-513" (trade name, manufactured by Catalyst Chemical Industry Co., Ltd., γ-butyrolactone dispersion having a solid component concentration of 30%) which is a silicon oxide-titanium oxide composite particle were mixed to prepare a composition 1. In the same manner as in Example 17, (1) formation of cured film, (2) evaluation of cracking resistance of cured film, (3) measurement of refractive index of cured film, and (4) determination of transmittance of cured film were performed. The evaluation results are shown in Table 5.

TABLE 5

|  |  | Evaluation of crack resistance | | Refractive index | Light transmittance per 1 μm of film thickness |
|---|---|---|---|---|---|
|  |  | Film thickness of 0.3 μm | Film thickness of 0.5 μm | | |
| Example 17 | Polymetalloxane (TP-1) solution | 4 | 3 | 1.65 | 92% |
| Example 18 | Polymetalloxane (TP-2) solution | 5 | 4 | 1.75 | 94% |
| Example 19 | Polymetalloxane (TP-3) solution | 5 | 4 | 1.78 | 95% |
| Example 20 | Polymetalloxane (TP-4) solution | 4 | 3 | 1.68 | 94% |
| Example 21 | Polymetalloxane (TP-5) solution | 5 | 5 | 1.92 | 97% |
| Example 22 | Polymetalloxane (TP-6) solution | 5 | 5 | 1.92 | 98% |
| Example 23 | Polymetalloxane (TP-7) solution | 5 | 5 | 1.89 | 98% |
| Example 24 | Polymetalloxane (TP-8) solution | 5 | 5 | 1.88 | 97% |
| Example 25 | Polymetalloxane (TP-9) solution | 5 | 5 | 1.75 | 97% |
| Example 26 | Polymetalloxane (TP-10) solution | 5 | 5 | 1.88 | 97% |
| Example 27 | Polymetalloxane (TP-11) solution | 5 | 5 | 1.89 | 98% |
| Example 28 | Polymetalloxane (TP-12) solution | 5 | 5 | 1.89 | 98% |
| Example 29 | Polymetalloxane (TP-13) solution | 5 | 5 | 1.87 | 97% |
| Example 30 | Polymetalloxane (ZP-1) solution | 5 | 5 | 1.72 | 98% |
| Example 31 | Polymetalloxane (ZP-2) solution | 5 | 5 | 1.68 | 98% |
| Example 32 | Polymetalloxane (ZP-3) solution | 5 | 5 | 1.72 | 98% |
| Comparative Example 1 | Polymetalloxane (TP-14) solution | 2 | 1 | 1.65 | 85% |
| Comparative Example 2 | Polymetalloxane (TP-15) solution | 2 | 1 | 1.85 | 85% |
| Comparative Example 3 | Polysiloxane (SP-1) solution | 5 | 5 | 1.63 | 85% |
| Comparative Example 4 | Metal compound particle-containing polysiloxane (SP-2) solution | 5 | 5 | 1.75 | 95% |
| Example 33 | Composition 1 | 5 | 5 | 1.96 | 96% |

Example 34

A member having a portion in which a transparent conductive film (I), a polymetalloxane cured film (II), a silicon oxide thin film (III) and/or a transparent pressure-sensitive adhesive thin film (IV) were laminated on the upper surface of a transparent underlying base material was fabricated, and (5) visibility of the transparent conductive film was evaluated.

(5) Evaluation of Visibility of Transparent Conductive Film (5a) Fabrication of Member (5a-1) Formation of Transparent Conductive Film Pattern On a chemically strengthened glass substrate having a thickness of 1.1 mm serving as a transparent underlying base material, sputtering was performed using ITO serving as a transparent conductive film (I) as a target to form an ITO film having a film thickness of 50 nm. Subsequently, a positive photoresist (OFPR-800, manufactured by Tokyo Ohka Kogyo Co., Ltd.) was spin-coated on the transparent conductive film (I) using a spin coater (1H-360S, manufactured by Mikasa Co., Ltd.) and heated at 100° C. for 2 minutes using a hot plate (SCW-636, manufactured by Dainippon Screen Mfg. Co., Ltd.) to form a prebaked film. The obtained prebaked film of the photoresist was exposed in a dose of 1,000 J/m$^2$ with a gap of 100 μm through a mask using PLA and an ultrahigh pressure mercury lamp as a light source. Thereafter, using an automatic developing apparatus (AD-2000, manufactured by Takizawa Co., Ltd.), shower development with an aqueous 2.38 wt % solution of tetramethylammonium hydroxide (hereinafter abbreviated to TMAH) was performed for 90 seconds, followed by rinsing with water for 30 seconds and further patterning of the photoresist. Thereafter, ITO was etched with an HCl—HNO$_3$-based etching solution and the photoresist was removed with a stripping solution to fabricate a substrate including ITO (reference sign 2 in FIGS. 1 and 2) in which a first electrode and a part of a second electrode orthogonal to the first electrode are patterned (corresponding to a in FIG. 1).

(5a-2) Formation of Transparent Insulating Film

A negative photosensitive resin composition NS-E2000 (manufactured by Toray Industries, Inc.) was spin-coated on the substrate obtained in (5a-1) and then heated by a hot plate at 90° C. for 2 minutes to form a prebake film. The obtained prebake film was exposed in a dose of 2,000 J/m$^2$ with a gap of 100 μm through a mask. Thereafter, shower development with an aqueous 0.4 wt % TMAH solution for 90 seconds, followed by rinsing with water for 30 seconds.

Figure 2:
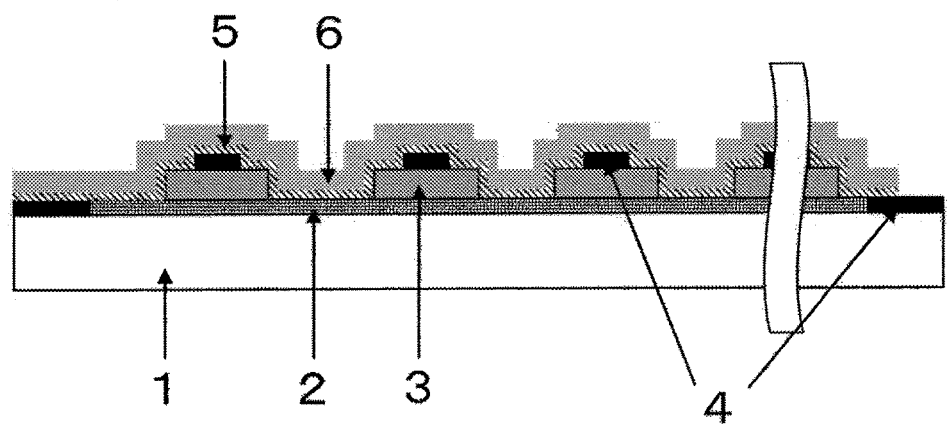
FIG. 2 is a schematic view showing a cross section of a substrate for evaluation of visibility of a transparent conductive film.

Next, curing was performed in the air at 230° C. for 1 hour to form a transparent insulating film (reference sign 3 in FIGS. 1 and 2) having a film thickness of 1.5 μm (corresponding to b in FIG. 1).

(5a-3) Fabrication of Molybdenum/Aluminum/Molybdenum (Hereinafter Abbreviated to MAM) Wiring By the same procedure as in (5a-1), except that molybdenum and aluminum were used as targets on the substrate obtained in (5a-2) and a mixed solution of $H_3PO_4/HNO_3/CH_3COOH/H_2O$ (=65/3/5/27) (weight ratio) was used as the etching solution, MAM wiring (reference sign 4 in FIGS. 1 and 2) was fabricated (corresponding to c of FIG. 1). The film thickness of MAM was adjusted to be 250 nm.

(5a-4) Formation of Polymetalloxane Cured Film (II)

On the substrate obtained in (5a-3), a polymetalloxane (TP-1) solution was pattern-coated by an inkjet coating apparatus and prebaked at 90° C. for 2 minutes. Next, curing was performed in the air at 230° C. for 1 hour to form a polymetalloxane (TP-1) cured film (II) (reference sign 5 in FIG. 2).

(5a-5) Formation of Silicon Oxide Thin Film (III)

Using a high-speed plasma CVD film forming apparatus (PD-270STL, manufactured by Samco Inc.), a silicon oxide thin film (III) (reference sign 6 in FIG. 2) was formed from tetraethoxysilane as a raw material. In that case, mask deposition was performed such that patterns of the silicon oxide thin film (III) and the thin film (II) containing the polymetalloxane-containing composition are superposed one upon another. The film thickness of the silicon oxide thin film (III) was 0.5 μm.

(5a-6) Sticking of Film with Transparent Pressure-Sensitive Adhesive

A PET film (HA-116; manufactured by Lintec Corporation, pressure-sensitive adhesive refractive index=1.47) provided with a pressure-sensitive adhesive and a hard coat on the opposite surface was stuck on a part of the substrate obtained in (5a-5) so as to prevent air entrainment to form a transparent pressure-sensitive adhesive layer (IV).

(5b) Evaluation of Visibility of Transparent Conductive Film

By observing from the back side of the substrate obtained in (5a-6), visibility of the transparent conductive film was evaluated according to the following 10 ranks. Ranks of 6 or more were rated as "pass".

10: No pattern is visible by staring at 3 cm under white fluorescent lamp.
9: Pattern is slightly visible by staring at 3 cm under white fluorescent lamp.
8: Pattern is visible a little by staring at 3 cm under the white fluorescent lamp.
7: Pattern is clearly visible by staring at 3 cm under white fluorescent lamp.
6: Pattern is slightly visible by usual visual confirmation at 3 cm under white fluorescent lamp.
5: Pattern is visible a little by usual visual confirmation at 3 cm under white fluorescent lamp.
4: Pattern is clearly visible by usual visual confirmation at 3 cm under white fluorescent lamp.
3: Pattern is slightly visible by usual visual confirmation under indoor light.
2: Pattern is visible a little by usual visual confirmation under indoor light.
1: Pattern is clearly visible by usual visual confirmation under indoor light.

(6) Evaluation of Corrosivity of Underlying Metal

A polymetalloxane cured film (II) was formed on a glass with MAM as the underlying metal formed on the entire surface by the method mentioned in (5a-4), and then a silicon oxide thin film (III) was formed by the method mentioned in (5a-5). After performing a test (pressure cooker cooker test, PCT test) in which a sample is left to stand in an oven (HAST CHAMBERE EHS-221MD, manufactured by Espec Corporation) at a temperature of 121° C., a humidity of 100%, and an atmospheric pressure of 2 atm for 20 hours, an occupied area ratio of defects of discoloration of MAM under the cured film due to corrosion was visually evaluated according to the following 11 ranks. Ranks of 7 or more were rated "pass".

10: Discolored area ratio of MAM under cured film is 0%, no change in appearance occurs in cured film itself.
9: Discolored area ratio of MAM under cured film is 1 to 3%, no change in appearance occurs in cured film itself.
8: Discolored area ratio of MAM under cured film is 4 to 6%, no change in appearance occurs in cured film itself.
7: Discolored area ratio of MAM under cured film is 7 to 9%, no change in appearance occurs in cured film itself.
6: Discolored area ratio of MAM under cured film is 10 to 15%, no change in appearance occurs in cured film itself.
5: Discolored area ratio of MAM under cured film is 16 to 20%, no change in appearance occurs in cured film itself.
4: Discolored area ratio of MAM under cured film is 21 to 30%, no change in appearance occurs in cured film itself.
3: Discolored area ratio of MAM under cured film is 31 to 50%, no change in appearance occurs in cured film itself.
2: Discolored area ratio of MAM under cured film is 51 to 70%, no change in appearance occurs in cured film itself.
1: Discolored area ratio of MAM under cured film is 71 to 100%, no change in appearance occurs in cured film itself.
0: Discolored area ratio of MAM under cured film is 100%, and discoloration and cracks occur in cured film itself.

Examples 35 to 49, Comparative Examples 5 to 8

(5) Evaluation of visibility of a transparent conductive film and (6) evaluation of a substrate metal were performed in the same manner as in Example 34 with the structure shown in Table 6. The evaluation results are shown in Table 6.

Example 50

(5) Evaluation of visibility of a transparent conductive film and (6) evaluation of an underlying metal were performed in the same manner as in Example 34, except that the composition 1 prepared in Example 33 was used in place of the polymetalloxane (TP-1) solution in (5a-3) formation of the polymetalloxane cured film (II). The evaluation results are shown in Table 6.

Example 51

(5) Evaluation of visibility of a transparent conductive film, and (6) evaluation of an underlying metal were performed in the same manner as in Example 40, except that (5a-5) the step of forming a silicon oxide thin film (III) was not performed. The evaluation results are shown in Table 6.

Example 52

(5) Evaluation of visibility of a transparent conductive film and (6) evaluation of an underlying metal were performed in the same manner as in Example 40, except that (5a-6) the step of sticking a film with a transparent pressure-sensitive adhesive was not performed. The evaluation results are shown in Table 6.

Example 53

(5) Evaluation of visibility of a transparent conductive film was performed in the same manner as in Example 40, except that a polyethylene terephthalate (hereinafter abbreviated to PET) base material having a thickness of 0.2 mm was used in place of the chemically tempered glass substrate in (5a-1) formation of a transparent conductive film pattern. The evaluation results are shown in Table 6.

Comparative Example 9

(5) Evaluation of visibility of a transparent conductive film and (6) evaluation of an underlying metal were performed in the same manner as in Example 40, except that (5a-4) the step of forming a polymetalloxane cured film (II) was not performed. The evaluation results are shown in Table 6.

TABLE 6

| | (5) Evaluation of visibility of transparent conductive film | | | | | | | |
|---|---|---|---|---|---|---|---|---|
| | (5a-1) Formation of transparent conductive film pattern | | | | (5a-2) Formation of transparent insulating film | (5a-3) MAM wiring | (5a-4) Polymetalloxane cured film (II) | |
| | Transparent underlying base material | | Transparent conductive thin film (I) | | | | | |
| | Type | Thickness | Type | Thickness | | | Type | Film thickness |
| Example 34 | Chemically tempered glass | 1.1 mm | ITO | 50 nm | Presence | Presence | Polymetalloxane (TP-1) | 0.10 μm |
| Example 35 | Chemically tempered glass | 1.1 mm | ITO | 50 nm | Presence | Presence | Polymetalloxane (TP-2) | 0.10 μm |
| Example 36 | Chemically tempered glass | 1.1 mm | ITO | 50 nm | Presence | Presence | Polymetalloxane (TP-3) | 0.10 μm |
| Example 37 | Chemically tempered glass | 1.1 mm | ITO | 50 nm | Presence | Presence | Polymetalloxane (TP-4) | 0.10 μm |
| Example 38 | Chemically tempered glass | 1.1 mm | ITO | 50 nm | Presence | Presence | Polymetalloxane (TP-5) | 0.10 μm |
| Example 39 | Chemically tempered glass | 1.1 mm | ITO | 50 nm | Presence | Presence | Polymetalloxane (TP-6) | 0.10 μm |
| Example 40 | Chemically tempered glass | 1.1 mm | ITO | 50 nm | Presence | Presence | Polymetalloxane (TP-7) | 0.10 μm |
| Example 41 | Chemically tempered glass | 1.1 mm | ITO | 50 nm | Presence | Presence | Polymetalloxane (TP-8) | 0.10 μm |
| Example 42 | Chemically tempered glass | 1.1 mm | ITO | 50 nm | Presence | Presence | Polymetalloxane (TP-9) | 0.10 μm |
| Example 43 | Chemically tempered glass | 1.1 mm | ITO | 50 nm | Presence | Presence | Polymetalloxane (TP-10) | 0.10 μm |
| Example 44 | Chemically tempered glass | 1.1 mm | ITO | 50 nm | Presence | Presence | Polymetalloxane (TP-11) | 0.10 μm |
| Example 45 | Chemically tempered glass | 1.1 mm | ITO | 50 nm | Presence | Presence | Polymetalloxane (TP-12) | 0.10 μm |
| Example 46 | Chemically tempered glass | 1.1 mm | ITO | 50 nm | Presence | Presence | Polymetalloxane (TP-13) | 0.10 μm |
| Example 47 | Chemically tempered glass | 1.1 mm | ITO | 50 nm | Presence | Presence | Polymetalloxane (ZP-1) | 0.10 μm |
| Example 48 | Chemically tempered glass | 1.1 mm | ITO | 50 nm | Presence | Presence | Polymetalloxane (ZP-2) | 0.10 μm |
| Example 49 | Chemically tempered glass | 1.1 mm | ITO | 50 nm | Presence | Presence | Polymetalloxane (ZP-3) | 0.10 μm |
| Comparative Example 5 | Chemically tempered glass | 1.1 mm | ITO | 50 nm | Presence | Presence | Polymetalloxane (TP-14) | 0.10 μm |
| Comparative Example 6 | Chemically tempered glass | 1.1 mm | ITO | 50 nm | Presence | Presence | Polymetalloxane (TP-15) | 0.10 μm |
| Comparative Example 7 | Chemically tempered glass | 1.1 mm | ITO | 50 nm | Presence | Presence | Polysiloxane (SP-1) | 0.10 μm |
| Comparative Example 8 | Chemically tempered glass | 1.1 mm | ITO | 50 nm | Presence | Presence | Metal compound particle-containing Polysiloxane (SP-2) | 0.10 μm |
| Example 50 | Chemically tempered glass | 1.1 mm | ITO | 50 nm | Presence | Presence | Composition 1 | 0.10 μm |
| Example 51 | Chemically tempered glass | 1.1 mm | ITO | 50 nm | Presence | Presence | Polymetalloxane (TP-7) | 0.10 μm |
| Example 52 | Chemically tempered glass | 1.1 mm | ITO | 50 nm | Presence | Presence | Polymetalloxane (TP-7) | 0.10 μm |
| Example 53 | PET | 1.1 mm | ITO | 50 nm | Presence | Presence | Polymetalloxane (TP-7) | 0.10 μm |
| Comparative Example 9 | Chemically tempered glass | 1.1 mm | ITO | 50 nm | Presence | Presence | — | |

TABLE 6-continued

| | (5) Evaluation of visibility of transparent conductive film | | | (6) Evaluation of underlying metal | | | | |
|---|---|---|---|---|---|---|---|---|
| | (5a-5) Silicon oxide thin film (III) | (5a-6) Film with transparent pressure-sensitive adhesive | (5b) Evaluation of visibility of transparent conductive film | Underlying metal | (5a-4) Polymetalloxane cured film (II) Type | Film thickness | (5a-5) Silicon oxide thin film (III) | Evaluation of underlying metal |
| Example 34 | 0.5 μm | Presence | 6 | MAM | Polymetalloxane (TP-1) | 0.10 μm | 0.5 μm | 10 |
| Example 35 | 0.5 μm | Presence | 7 | MAM | Polymetalloxane (TP-2) | 0.10 μm | 0.5 μm | 10 |
| Example 36 | 0.5 μm | Presence | 8 | MAM | Polymetalloxane (TP-3) | 0.10 μm | 0.5 μm | 10 |
| Example 37 | 0.5 μm | Presence | 6 | MAM | Polymetalloxane (TP-4) | 0.10 μm | 0.5 μm | 10 |
| Example 38 | 0.5 μm | Presence | 10 | MAM | Polymetalloxane (TP-5) | 0.10 μm | 0.5 μm | 10 |
| Example 39 | 0.5 μm | Presence | 10 | MAM | Polymetalloxane (TP-6) | 0.10 μm | 0.5 μm | 10 |
| Example 40 | 0.5 μm | Presence | 10 | MAM | Polymetalloxane (TP-7) | 0.10 μm | 0.5 μm | 10 |
| Example 41 | 0.5 μm | Presence | 10 | MAM | Polymetalloxane (TP-8) | 0.10 μm | 0.5 μm | 10 |
| Example 42 | 0.5 μm | Presence | 8 | MAM | Polymetalloxane (TP-9) | 0.10 μm | 0.5 μm | 10 |
| Example 43 | 0.5 μm | Presence | 10 | MAM | Polymetalloxane (TP-10) | 0.10 μm | 0.5 μm | 10 |
| Example 44 | 0.5 μm | Presence | 10 | MAM | Polymetalloxane (TP-11) | 0.10 μm | 0.5 μm | 10 |
| Example 45 | 0.5 μm | Presence | 10 | MAM | Polymetalloxane (TP-12) | 0.10 μm | 0.5 μm | 10 |
| Example 46 | 0.5 nm | Presence | 10 | MAM | Polymetalloxane (TP-13) | 0.10 μm | 0.5 μm | 10 |
| Example 47 | 0.5 μm | Presence | 7 | MAM | Polymetalloxane (ZP-1) | 0.10 μm | 0.5 μm | 10 |
| Example 48 | 0.5 μm | Presence | 7 | MAM | Polymetalloxane (ZP-2) | 0.10 μm | 0.5 μm | 10 |
| Example 49 | 0.5 μm | Presence | 7 | MAM | Polymetalloxane (ZP-3) | 0.10 μm | 0.5 μm | 10 |
| Comparative Example 5 | 0.5 μm | Presence | 6 | MAM | Polymetalloxane (TP-14) | 0.10 μm | 0.5 μm | 10 |
| Comparative Example 6 | 0.5 μm | Presence | 9 | MAM | Polymetalloxane (TP-15) | 0.10 μm | 0.5 μm | 10 |
| Comparative Example 7 | 0.5 μm | Presence | 4 | MAM | Polysiloxane (SP-1) | 0.10 μm | 0.5 μm | 10 |
| Comparative Example 8 | 0.5 μm | Presence | 7 | MAM | Metal compound particle-containing polysiloxane (SP-2) | 0.10 μm | 0.5 μm | 10 |
| Example 50 | 0.5 μm | Presence | 10 | MAM | Composition 1 | 0.10 μm | 0.5 μm | 10 |
| Example 51 | — | Presence | 10 | MAM | Polymetalloxane (TP-7) | 0.10 μm | — | 6 |
| Example 52 | 0.5 μm | — | 8 | MAM | Polymetalloxane (TP-7) | 0.10 μm | 0.5 μm | 10 |
| Example 53 | 0.5 μm | Presence | 10 | MAM | Polymetalloxane (TP-7) | 0.10 μm | 0.5 μm | — |
| Comparative Example 9 | 0.5 μm | Presence | 1 | MAM | — | | 0.5 μm | 8 |

Example 54

Dry etching of the polymetalloxane cured film formed on the substrate was performed, and the surface roughness Ra and the light transmittance after the dry etching were measured. Details are shown below. The measurement results are shown in Table 6.

(6-1) Preparation of Cured Film

A polymetalloxane (TP-05) solution was spin-coated on a 6-inch silicon wafer and a Tempax glass plate using a spin coater (1H-360S, manufactured by Mikasa Co., Ltd.) and heated at 100° C. for 3 minutes using a hotplate (SCW-636 manufactured by Dainippon Screen Mfg. Co., Ltd.) to prepare a prebake film. Thereafter, the film was cured by using a hot plate at 300° C. for 5 minutes to prepare a cured film each having a film thicknesses of 0.5 μm. The film thickness was measured using a spectroscopic reflectometer (Lambda Ace STM602, manufactured by Dainippon Screen Mfg. Co., Ltd.).

(6-2) Measurement of Refractive Index

With respect to the cured film formed on a silicon wafer, the temperature during measurement was set at 22° C., and the polarization state change of the reflected light from the cured film was measured using a spectroscopic ellipsometer (FE5000, manufactured by Otsuka Electronics Co., Ltd.) to obtain a phase difference with the incident light and a spectrum of an amplitude reflectance. By fitting the dielectric function of the calculation model such that it approaches the obtained spectrum, a refractive index spectrum was obtained. By reading the refractive index value at a wavelength of 550 nm from the refractive index spectrum, the value was regarded as the refractive index of the cured film.

(6-3) Measurement of Light Transmittance of Cured Film

Using a spectrophotometer (MultiSpec-1500, manufactured by Shimadzu Corporation), an ultraviolet-visible absorption spectrum of a Tempax glass plate was measured, and this spectrum was used as a reference. Subsequently, the ultraviolet-visible absorption spectrum of the cured film formed on the Tempax glass plate was measured, and the ultraviolet-visible absorption spectrum of the cured film was calculated from the difference from the reference. Using the obtained ultraviolet-visible absorption spectrum and film thickness, the light transmittance per 1 μm of the film thickness at a wavelength of 400 nm of the cured film was calculated.

(6-4) Dry Etching

Using a reactive ion etching apparatus (RIE-10N manufactured by Samco Inc.), the cured film formed on the Tempax glass plate was dry-etched with a mixed gas of $CF_4$ (tetrafluoromethane) and oxygen as a process gas. The dry etching conditions are as follows: a gas mixture ratio $CF_4$: oxygen of 80:20, a gas flow rate of 50 sccm, an output of 199 W, an internal pressure of 10 Pa, and a treatment time of 2 minutes.

(6-5) Measurement of Surface Roughness after Dry Etching

The surface of the cured film after the dry etching treatment was scanned by a scanning probe microscope (Dimension Icon, manufactured by Bruker Corporation) to obtain a three-dimensional stereoscopic image of the cured film surface. The obtained image was cut to obtain a contour curve of a cross section of the cured film. An arithmetic average roughness Ra was obtained by calculating the obtained contour curve based on JIS B 0601:2013.

(6-6) Measurement of Light Transmittance after Dry Etching

Using a spectrophotometer (MultiSpec-1500, manufactured by Shimadzu Corporation), an ultraviolet-visible absorption spectrum of the Tempax glass plate was measured, and this spectrum was used as a reference. Subsequently, the ultraviolet-visible absorption spectrum of the cured film formed on the Tempax glass plate after the dry etching treatment was measured and the ultraviolet-visible absorption spectrum of the cured film after the dry etching treatment was calculated from the difference from the reference. Using the obtained ultraviolet-visible absorption spectrum and film thickness, the light transmittance per 1 μm of the film thickness at the wavelength of 400 nm of the cured film after the dry etching treatment was calculated.

These results are shown in Table 7.

Examples 55 to 65, Comparative Examples 10 to 11

With respect to the solutions shown in Table 7, (6-1) formation of a cured film, (6-2) measurement of a refractive index, (6-3) measurement of a light transmittance of a cured film, (6-4) dry etching, (6-5) measurement of surface roughness after dry etching, and (6-6) measurement of a light transmittance after dry etching were performed in the same manner as in Example 54. The evaluation results are shown in Table 7.

TABLE 7

| | Solution | Cured film properties | | | Surface roughness Ra after dry etching | Light transmittance of cured film after dry etching |
|---|---|---|---|---|---|---|
| | | Film thickness | Refractive index | Light transmittance per 1 μm of film thickness | | |
| Example 54 | Polymetalloxane (TP-5) solution | 0.5 μm | 1.92 | 97% | 2 nm | 97% |
| Example 55 | Polymetalloxane (TP-6) solution | 0.5 μm | 1.92 | 98% | 2 nm | 98% |
| Example 56 | Polymetalloxane (TP-7) solution | 0.5 μm | 1.89 | 98% | 2 nm | 98% |
| Example 57 | Polymetalloxane (TP-8) solution | 0.5 μm | 1.88 | 97% | 3 nm | 97% |
| Example 58 | Polymetalloxane (TP-9) solution | 0.5 μm | 1.75 | 97% | 4 nm | 97% |
| Example 59 | Polymetalloxane (TP-10) solution | 0.5 μm | 1.88 | 97% | 2 nm | 97% |
| Example 60 | Polymetalloxane (TP-11) solution | 0.5 μm | 1.89 | 98% | 2 nm | 98% |
| Example 61 | Polymetalloxane (TP-12) solution | 0.5 μm | 1.89 | 98% | 2 nm | 98% |
| Example 62 | Polymetalloxane (TP-13) solution | 0.5 μm | 1.87 | 97% | 2 nm | 97% |
| Example 63 | Polymetalloxane (ZP-1) solution | 0.5 μm | 1.72 | 98% | 2 nm | 98% |
| Example 64 | Polymetalloxane (ZP-2) solution | 0.5 μm | 1.68 | 98% | 3 nm | 98% |
| Example 65 | Polymetalloxane (ZP-3) solution | 0.5 μm | 1.72 | 98% | 2 nm | 98% |
| Comparative Example 10 | Polysiloxane (SP-1) solution | 0.5 μm | 1.63 | 85% | 3 nm | 85% |
| Comparative Example 11 | Metal compound particle-containing polysiloxane (SP-2) solution | 0.5 μm | 1.75 | 95% | 50 nm | 80% |

In Comparative Example 10, a cured film was formed using a polysiloxane (SP-1) solution. Since the polysiloxane (SP-1) has an anthracenyl group with a high refractive index, a high refractive index of 1.63 could be realized. However, since the anthracenyl group has an absorption in a visible light region due to its origin, the transmittance became 85% and high transparency required for the microlens could not be obtained.

In Comparative Example 11, a cured film was formed using a solution of a metal compound particle-containing polysiloxane (SP-2). Since titanium oxide particles with a high refractive index were used, a very high refractive index of 1.75 could be realized. However, during dry etching, the reactivity with the etching gas varies depending on the titanium oxide particles and the polysiloxane component, so that a difference in dry etching rate locally occurred. Therefore, the surface of the cured film was roughened, and the arithmetic average roughness Ra became 50 nm. When the surface of the cured film is roughened, light is scattered, so that the transmittance after the dry etching became 80%, thus failing to obtain high transparency required for the microlens.

Example 66

A polymetalloxane solution (TP-7) was spin-coated on a 6-inch silicon wafer using a spin coater (1H-360S manufactured by Mikasa Corporation) and heated at 100° C. for 3 minutes using a hot plate (SCW-636, manufactured by Dainippon Screen Mfg. Co., Ltd.) to form a prebaked film. Thereafter, the prebaked film was cured by using a hot plate at 300° C. for 5 minutes to form a cured film containing a polymetalloxane having a film thickness of 0.5 μm.

Thereafter, a positive type photoresist (OFPR-800, manufactured by Tokyo Ohka Kogyo Co., Ltd.) was spin-coated on the cured film containing a polymetalloxane and then heated at 100° C. for 2 minutes using a hot plate to form a photoresist layer. Thereafter, pattern exposure was performed through a mask using an i-line stepper (NSR-i9C, manufactured by Nikon Corporation). As a mask, a mask designed to obtain a 2 μm dot pattern was used.

Thereafter, using an automatic developing apparatus (AD-2000, manufactured by Takizawa Co., Ltd.), shower development with an aqueous 2.38 wt % solution of tetramethylammonium hydroxide as a developer was performed for 90 seconds, followed by rinsing with water for 30 seconds to obtain a 2 μm dot-shaped photoresist pattern. Thereafter, the photoresist pattern was melted by heating at 120° C. for 5 minutes using a hot plate.

The cured film containing a photoresist pattern and a polymetalloxane was etched using a reactive ion etching apparatus (RIE-10N, manufactured by Samco Inc.) and then the entire surface was dry-etched with a mixed gas of $CF_4$ (tetrafluoromethane) and oxygen as a process gas to obtain a microlens pattern containing a polymetalloxane. The dry etching conditions are as follows: a gas mixture ratio $CF_4$: oxygen of 80:20, a gas flow rate of 50 sccm, an output of 199 W, an internal pressure of 10 Pa, and a treatment time of 5 minutes.

Observation of the obtained microlens pattern using a scanning electron microscope (S-4800, manufactured by Hitachi High-Tech Technologies Corporation) revealed that it was a smooth microlens pattern without surface roughness.

The arithmetic mean surface roughness of the microlens pattern was determined by the following method. The surface of the microlens pattern was scanned by a scanning probe microscope (Dimension Icon, manufactured by Bruker Corporation) to obtain a three-dimensional stereoscopic image. The obtained image was cut to obtain a contour curve of a microlens cross section. The curvature of the microlens was removed from the contour curve, and a surface roughness curve was obtained. From the surface roughness curve, the arithmetic average roughness Ra was obtained by calculation based on JIS B 0601:2013. The arithmetic mean surface roughness Ra of the obtained microlens pattern was 4 nm.

REFERENCE SIGNS LIST

1: Transparent underlying substrate
2: Transparent conductive thin film (I)
3: Insulating film
4: MAM wiring
5: Cured film (II) obtained from polymetalloxane or composition thereof
6: Silicon oxide thin film (III)

The invention claimed is:

1. A polymetalloxane formed by polycondensation of a compound represented by general formula (2) or a hydrosylate thereof:

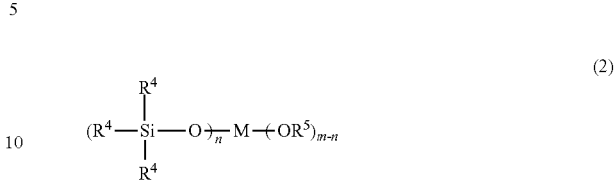

wherein
$R^4$ is selected from all methyl or all ethyl,
$R^5$ is selected from a hydrogen atom or an alkyl group having 1 to 4 carbon atoms, when plural $R^4$ and $R^5$ exist, they may be the same or different,
M represents a metal atom selected from the group consisting of Ti, Zr and Sn,
m is an integer indicating a valence of a metal atom M, and
n is an integer of 1 to (m−1),
where the polymetalloxane consists of a constituent unit represented by the following general formula (1) as a repeating unit and having a weight average molecular weight of 10,000 or more:

wherein:
$R^1$ is a hydroxy group, an alkoxy group having 1 to 4 carbon atoms or an ($R^3_3$SiO—) group selected from the group consisting of a trimethylsiloxy group and a triethylsiloxy group,
$R^2$ is selected from a hydrogen atom, an alkyl group having 1 to 4 carbon atoms, or a group having a metalloxane bond, and
wherein:
when plural $R^1$, $R^2$, and $R^3$ exist, they may be the same or different,
M represents a metal atom selected from the group consisting of Ti, Zr and Sn,
m is an integer indicating a valence of the metal atom M,
a is an integer of 1 to (m−2), and
content of the ($R^3_3$SiO—) group, represented by the ratio of the number of mols of Si atoms to the number of mols of M atoms of the polymetalloxane, is 10 mol % or more and 100 mol % or less.

2. The polymetalloxane according to claim 1, wherein at least one of $R^1$ in the polymetalloxane is a hydroxy group.

3. A composition comprising the polymetalloxane according to claim 1 and a solvent selected from the group consisting of alcohols, esters, ethers and ketones.

4. A composition comprising the polymetalloxane according to claim 1 and inorganic particles.

5. A cured film of the polymetalloxane according to claim 1.

6. A cured film of the composition according to claim 3.

7. A method for producing a cured film, which comprises the step of heating the polymetalloxane according to claim 1.

8. A member comprising the cured film according to claim 5.

9. The member according to claim 8, wherein the member is a lens.

10. An electronic component comprising the member according to claim 8.

11. The electronic component according to claim 10, which is a touch sensor, an image sensor, an organic EL element or an organic EL lighting.

12. A building material comprising the polymetalloxane according to claim 1.

13. A column packed with the polymetalloxane according to claim 1.

14. A radionuclide generator comprising the column according to claim 13.

15. A method for producing a cured film, which comprises a step of heating the composition according to claim 3.

16. The polymetalloxane according to claim 1, wherein the polymetalloxane has a weight average molecular weight of 46,000 or more.

17. The polymetalloxane according to claim 16, wherein when the polymetalloxane is heated at a temperature of 300° C. for 5 minutes to obtain a cured film and a refractive index of the cured film at a wavelength of 550 nm is measured, the refractive index is 1.87 or more and 2.10 or less.

* * * * *